(12) United States Patent
Benjamin et al.

(10) Patent No.: US 10,512,758 B2
(45) Date of Patent: Dec. 24, 2019

(54) CATHETER SYSTEM AND METHODS OF USING SAME

(71) Applicant: Endologix, Inc., Irvine, CA (US)

(72) Inventors: Joshua Benjamin, Aliso Viejo, CA (US); Stefan Schreck, Fallbrook, CA (US)

(73) Assignee: Endologix, Inc., Irvine, CA (US)

( * ) Notice: Subject to any disclaimer, the term of this patent is extended or adjusted under 35 U.S.C. 154(b) by 242 days.

(21) Appl. No.: 15/639,028

(22) Filed: Jun. 30, 2017

(65) Prior Publication Data

US 2017/0296791 A1    Oct. 19, 2017

Related U.S. Application Data

(63) Continuation of application No. 13/544,426, filed on Jul. 9, 2012, now Pat. No. 9,700,701, which is a
(Continued)

(51) Int. Cl.
*A61F 2/06*      (2013.01)
*A61M 25/06*     (2006.01)
(Continued)

(52) U.S. Cl.
CPC .......... *A61M 25/0662* (2013.01); *A61F 2/95* (2013.01); *A61M 25/0097* (2013.01);
(Continued)

(58) Field of Classification Search
CPC .......... A61M 25/0662; A61M 25/0097; A61M 2025/0681; A61M 2025/0079;
(Continued)

(56) References Cited

U.S. PATENT DOCUMENTS

| 519,928 A   | 5/1894 | Schanck |
|-------------|--------|---------|
| 1,065,935 A | 7/1913 | Gail    |

(Continued)

FOREIGN PATENT DOCUMENTS

| CA | 2220141 | 11/1996 |
|----|---------|---------|
| CA | 2287406 | 12/1997 |

(Continued)

OTHER PUBLICATIONS

US 5,690,647 A, 11/1997, Osborne (withdrawn)
(Continued)

*Primary Examiner* — Amy R Weisberg
(74) *Attorney, Agent, or Firm* — Foley & Lardner LLP

(57) ABSTRACT

Some embodiments are directed to a catheter system comprising an introducer having a main body, an introducer sheath projecting from the main body, and a first seal supported within the introducer and a catheter having a main body, an outer sheath projecting from the main body, a second seal supported within the catheter, and an inner core configured to be advanced axially through the main body, the second seal, and the outer sheath. The introducer can be configured to be selectively engageable with the catheter so that the catheter can be selectively and removably linked with the introducer in the axial direction. The catheter system can also be configured such that, when the introducer and the catheter are linked, the catheter can be rotatable relative to the introducer. The introducer can be configured to radially restrain an endoluminal prosthesis.

21 Claims, 18 Drawing Sheets

Related U.S. Application Data continuation of application No. 12/496,446, filed on Jul. 1, 2009, now Pat. No. 8,216,295.

(60) Provisional application No. 61/077,429, filed on Jul. 1, 2008, provisional application No. 61/184,742, filed on Jun. 5, 2009.

(51) Int. Cl.
    *A61F 2/95*     (2013.01)
    *A61M 25/00*     (2006.01)
    *A61F 2/966*     (2013.01)

(52) U.S. Cl.
    CPC ....... *A61F 2/966* (2013.01); *A61F 2002/9517* (2013.01); *A61M 2025/0006* (2013.01); *A61M 2025/0079* (2013.01); *A61M 2025/0681* (2013.01)

(58) Field of Classification Search
    CPC .............. A61M 2025/0006; A61F 2/95; A61F 2002/9517; A61F 2/966
    See application file for complete search history.

(56) References Cited

U.S. PATENT DOCUMENTS

| | | | |
|---|---|---|---|
| 2,127,903 | A | 8/1938 | Bowen |
| 2,335,333 | A | 11/1943 | Wysong |
| 2,437,542 | A | 5/1944 | Krippendorf |
| 2,845,959 | A | 8/1958 | Sidebotham |
| 2,990,605 | A | 7/1961 | Demsyk |
| 3,029,819 | A | 4/1962 | Starks |
| 3,096,560 | A | 7/1963 | Liebig |
| 3,245,703 | A | 4/1966 | Manly |
| 3,805,301 | A | 4/1974 | Liebig |
| 3,994,149 | A | 11/1976 | Dahlman |
| 4,362,156 | A | 12/1982 | Feller, Jr. et al. |
| 4,473,067 | A | 9/1984 | Schiff |
| 4,497,074 | A | 2/1985 | Ray et al. |
| 4,501,263 | A | 2/1985 | Harbuck |
| 4,503,568 | A | 3/1985 | Madras |
| 4,525,157 | A | 6/1985 | Vaillancourt |
| 4,562,596 | A | 1/1986 | Kornberg |
| 4,580,568 | A | 4/1986 | Gianturco |
| 4,592,754 | A | 6/1986 | Gupte et al. |
| 4,617,932 | A | 10/1986 | Kornberg |
| 4,723,550 | A | 2/1988 | Bales et al. |
| 4,723,938 | A | 2/1988 | Goodin et al. |
| 4,756,307 | A | 7/1988 | Crownshield |
| 4,768,507 | A | 9/1988 | Fischell et al. |
| 4,772,266 | A | 9/1988 | Groshong |
| 4,795,465 | A | 1/1989 | Marten |
| 4,800,882 | A | 1/1989 | Gianturco |
| 4,816,028 | A | 3/1989 | Kapadia et al. |
| 4,840,940 | A | 6/1989 | Sottiurai |
| 4,856,516 | A | 8/1989 | Hillstead |
| 4,878,906 | A | 11/1989 | Lindemann et al. |
| 4,907,336 | A | 3/1990 | Gianturco |
| 4,917,668 | A | 4/1990 | Haindl |
| 4,922,905 | A | 5/1990 | Strecker |
| 4,960,412 | A | 10/1990 | Fink |
| 4,978,334 | A | 12/1990 | Toye et al. |
| 4,981,478 | A | 1/1991 | Evard et al. |
| 4,981,947 | A | 1/1991 | Tomagou et al. |
| 4,994,069 | A | 2/1991 | Ritchrt et al. |
| 4,994,071 | A | 2/1991 | MacGregor |
| 5,019,090 | A | 5/1991 | Pinchuk |
| 5,026,377 | A | 6/1991 | Burton et al. |
| 5,035,706 | A | 7/1991 | Giantureo et al. |
| 5,064,414 | A | 11/1991 | Revane |
| 5,064,435 | A | 11/1991 | Porter |
| 5,078,726 | A | 1/1992 | Kreamer |
| 5,084,010 | A | 1/1992 | Plaia et al. |
| 5,098,392 | A | 3/1992 | Fleischhacker et al. |
| 5,098,395 | A | 3/1992 | Fields |
| 5,104,399 | A | 4/1992 | Lazarus |
| 5,108,380 | A | 4/1992 | Herlitze et al. |
| 5,108,424 | A | 4/1992 | Hoffman, Jr. et al. |
| 5,116,349 | A | 5/1992 | Aranyi |
| 5,123,917 | A | 6/1992 | Lee |
| 5,133,732 | A | 7/1992 | Wiktor |
| 5,135,535 | A | 8/1992 | Kramer |
| 5,135,536 | A | 8/1992 | Hillstead |
| 5,137,519 | A | 8/1992 | Littrell et al. |
| 5,141,497 | A | 8/1992 | Erskine |
| 5,151,105 | A | 9/1992 | Kwan-Gett |
| 5,156,619 | A | 10/1992 | Ehrenfeld |
| 5,178,634 | A | 1/1993 | Martinez |
| 5,186,712 | A | 2/1993 | Kelso et al. |
| 5,195,978 | A | 3/1993 | Schiffer |
| 5,195,980 | A | 3/1993 | Catlin |
| 5,197,976 | A | 3/1993 | Herweck et al. |
| 5,201,757 | A | 4/1993 | Heyn et al. |
| 5,203,774 | A | 4/1993 | Gilson et al. |
| 5,205,829 | A | 4/1993 | Lituchy |
| 5,211,658 | A | 5/1993 | Clouse |
| 5,222,969 | A | 6/1993 | Gillis |
| 5,250,036 | A | 10/1993 | Farivar |
| 5,256,141 | A | 10/1993 | Gancheff et al. |
| 5,263,932 | A | 11/1993 | Jang |
| 5,267,982 | A | 12/1993 | Sylvanowicz |
| 5,275,622 | A | 1/1994 | Lazarus et al. |
| 5,279,592 | A | 1/1994 | Amor et al. |
| 5,282,824 | A | 2/1994 | Gianturco |
| 5,282,860 | A | 2/1994 | Matsuno et al. |
| 5,290,310 | A | 3/1994 | Makower et al. |
| 5,304,200 | A | 4/1994 | Spaulding |
| 5,314,444 | A | 5/1994 | Gianturco |
| 5,314,472 | A | 5/1994 | Fontaine |
| 5,316,023 | A | 5/1994 | Palmaz et al. |
| 5,320,602 | A | 6/1994 | Karpeil |
| 5,324,306 | A | 6/1994 | Makower et al. |
| 5,330,500 | A | 7/1994 | Song |
| 5,334,157 | A | 8/1994 | Klein et al. |
| 5,342,387 | A | 8/1994 | Summers |
| 5,350,397 | A | 9/1994 | Palermo et al. |
| 5,354,308 | A | 10/1994 | Simon et al. |
| 5,360,443 | A | 11/1994 | Barone et al. |
| 5,366,504 | A | 11/1994 | Andersen et al. |
| 5,370,683 | A | 12/1994 | Fontaine |
| 5,376,077 | A | 12/1994 | Gomringer |
| 5,383,892 | A | 1/1995 | Cardon et al. |
| 5,387,235 | A | 2/1995 | Chuter |
| 5,389,087 | A | 2/1995 | Miraki |
| 5,391,152 | A * | 2/1995 | Patterson .......... A61M 25/0097 604/165.04 |
| 5,397,310 | A | 3/1995 | Chu et al. |
| 5,397,355 | A | 3/1995 | Marin et al. |
| 5,403,283 | A | 4/1995 | Luther |
| 5,403,341 | A | 4/1995 | Solar |
| 5,405,323 | A | 4/1995 | Rogers et al. |
| 5,405,377 | A | 4/1995 | Cragg |
| 5,405,378 | A | 4/1995 | Strecker |
| 5,415,664 | A | 5/1995 | Pinchuk |
| 5,423,886 | A | 6/1995 | Arru et al. |
| 5,425,765 | A | 6/1995 | Tiefenbrun et al. |
| 5,443,477 | A | 8/1995 | Marin et al. |
| 5,443,498 | A | 8/1995 | Fontaine |
| 5,443,500 | A | 8/1995 | Sigwart |
| 5,453,090 | A | 9/1995 | Martinez et al. |
| 5,456,713 | A | 10/1995 | Chuter |
| 5,458,615 | A | 10/1995 | Klemm et al. |
| 5,462,530 | A | 10/1995 | Jang |
| 5,464,449 | A | 11/1995 | Ryan et al. |
| 5,464,450 | A | 11/1995 | Buscemi et al. |
| 5,464,499 | A | 11/1995 | Moslehi et al. |
| 5,472,417 | A | 12/1995 | Martin et al. |
| 5,484,444 | A | 1/1996 | Braunschweiler et al. |
| 5,489,295 | A | 2/1996 | Piplani et al. |
| 5,496,365 | A | 3/1996 | Sgro |
| 5,505,710 | A | 4/1996 | Dorsey, III |
| 5,507,727 | A | 4/1996 | Crainich |
| 5,507,767 | A | 4/1996 | Maeda et al. |

(56) References Cited

U.S. PATENT DOCUMENTS

| | | |
|---|---|---|
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,152 A | 8/1996 | Funderburk et al. |
| 5,545,211 A | 8/1996 | An et al. |
| 5,549,635 A | 8/1996 | Solar |
| 5,554,118 A | 9/1996 | Jang |
| 5,554,181 A | 9/1996 | Das |
| 5,562,697 A | 10/1996 | Christiansen |
| 5,562,726 A | 10/1996 | Chuter |
| 5,562,728 A | 10/1996 | Lazarus et al. |
| 5,571,169 A | 11/1996 | Plaia et al. |
| 5,571,172 A | 11/1996 | Chin |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,195 A | 1/1997 | Taheri et al. |
| 5,591,197 A | 1/1997 | Orth et al. |
| 5,591,198 A | 1/1997 | Boyle et al. |
| 5,591,226 A | 1/1997 | Trerotola et al. |
| 5,591,228 A | 1/1997 | Edoga |
| 5,591,229 A | 1/1997 | Parodi |
| 5,591,230 A | 1/1997 | Horn et al. |
| 5,593,417 A | 1/1997 | Rhodes |
| 5,599,305 A | 2/1997 | Hermann et al. |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,755 A | 5/1997 | Heller et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,634,928 A | 6/1997 | Fischell et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,653,748 A | 8/1997 | Strecker |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,671 A | 10/1997 | Inoue |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,697,971 A | 12/1997 | Fischell et al. |
| 5,700,269 A | 12/1997 | Pinchuk et al. |
| 5,707,354 A | 1/1998 | Salmon et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,725,519 A | 3/1998 | Penner et al. |
| 5,733,267 A | 3/1998 | Del Toro |
| 5,733,325 A | 3/1998 | Robinson et al. |
| 5,738,660 A | 4/1998 | Luther |
| 5,738,674 A | 4/1998 | Williams et al. |
| 5,741,233 A | 4/1998 | Riddle et al. |
| 5,746,766 A | 5/1998 | Edoga |
| 5,746,776 A | 5/1998 | Smith et al. |
| 5,749,880 A | 5/1998 | Banes et al. |
| 5,749,921 A | 5/1998 | Lenker et al. |
| 5,755,735 A | 5/1998 | Richter et al. |
| 5,755,770 A | 5/1998 | Ravenscroft |
| 5,755,771 A | 5/1998 | Penn et al. |
| 5,755,777 A | 5/1998 | Chuter |
| 5,765,682 A | 6/1998 | Bley et al. |
| 5,766,203 A | 6/1998 | Imran et al. |
| 5,769,885 A | 6/1998 | Quiachon et al. |
| 5,769,887 A | 6/1998 | Brown et al. |
| 5,772,636 A | 6/1998 | Brimhall et al. |
| 5,776,142 A | 7/1998 | Gunderson |
| 5,782,807 A | 7/1998 | Falvai et al. |
| 5,782,817 A | 7/1998 | Frenzel et al. |
| 5,782,855 A | 7/1998 | Lau et al. |
| 5,782,909 A | 7/1998 | Quiachon et al. |
| 5,788,707 A | 8/1998 | Del Toro et al. |
| 5,797,952 A | 8/1998 | Klein |
| 5,800,456 A | 9/1998 | Maeda et al. |
| 5,800,508 A | 9/1998 | Goicoechea et al. |
| 5,800,517 A | 9/1998 | Anderson et al. |
| 5,800,526 A | 9/1998 | Anderson et al. |
| 5,800,540 A | 9/1998 | Chin |
| 5,810,836 A | 9/1998 | Hussein et al. |
| 5,810,873 A | 9/1998 | Morales |
| 5,817,100 A | 10/1998 | Igaki |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,053 A | 10/1998 | Khosravi et al. |
| 5,843,046 A | 12/1998 | Motisi et al. |
| 5,843,092 A | 12/1998 | Heller et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |

(56) References Cited

U.S. PATENT DOCUMENTS

| | | |
|---|---|---|
| 5,860,998 A | 1/1999 | Robinson et al. |
| 5,865,844 A | 2/1999 | Plaia et al. |
| 5,867,432 A | 2/1999 | Toda |
| 5,868,783 A | 2/1999 | Tower |
| 5,871,536 A | 2/1999 | Lazarus |
| 5,876,432 A | 3/1999 | Lau et al. |
| 5,879,321 A | 3/1999 | Hill |
| 5,879,333 A | 3/1999 | Smith |
| 5,879,334 A | 3/1999 | Brimhall |
| 5,879,366 A | 3/1999 | Shaw et al. |
| 5,885,217 A | 3/1999 | Gisselberg et al. |
| 5,891,193 A | 4/1999 | Robinson et al. |
| 5,893,868 A | 4/1999 | Hanson et al. |
| 5,893,887 A | 4/1999 | Jayaraman |
| 5,902,334 A | 5/1999 | Dwyer et al. |
| 5,906,619 A | 5/1999 | Olson et al. |
| 5,906,640 A | 5/1999 | Penn et al. |
| 5,906,641 A | 5/1999 | Thompson et al. |
| 5,910,145 A | 6/1999 | Fischell et al. |
| 5,911,700 A | 6/1999 | Mozsary et al. |
| 5,911,710 A | 6/1999 | Barry et al. |
| 5,911,752 A | 6/1999 | Dustrude et al. |
| 5,916,263 A | 6/1999 | Goicoceha et al. |
| 5,919,225 A | 7/1999 | Lau et al. |
| 5,925,075 A | 7/1999 | Myers et al. |
| 5,925,076 A | 7/1999 | Inoue |
| 5,928,279 A | 7/1999 | Shannon et al. |
| 5,935,135 A | 8/1999 | Bramfitt et al. |
| 5,935,161 A | 8/1999 | Robinson et al. |
| 5,938,696 A | 8/1999 | Goicoechea et al. |
| 5,948,018 A | 9/1999 | Dereume et al. |
| 5,954,729 A | 9/1999 | Bachmann et al. |
| 5,957,973 A | 9/1999 | Quiachon et al. |
| 5,961,546 A | 10/1999 | Robinson et al. |
| 5,961,548 A | 10/1999 | Shmulewitz |
| 5,971,958 A | 10/1999 | Zhang |
| 5,976,153 A | 11/1999 | Fischell et al. |
| 5,976,155 A | 11/1999 | Foreman et al. |
| 5,997,562 A | 12/1999 | Zadno-Azizi et al. |
| 6,001,125 A | 12/1999 | Golds et al. |
| 6,004,294 A | 12/1999 | Brimhall et al. |
| 6,004,347 A | 12/1999 | McNamara et al. |
| 6,004,348 A | 12/1999 | Banas et al. |
| 6,017,363 A | 1/2000 | Hojeibane |
| 6,019,777 A | 2/2000 | Mackenzie |
| 6,019,785 A | 2/2000 | Strecker |
| 6,027,508 A | 2/2000 | Ren et al. |
| 6,027,779 A | 2/2000 | Campbell et al. |
| 6,027,811 A | 2/2000 | Campbell et al. |
| 6,030,414 A | 2/2000 | Taheri |
| 6,030,415 A | 2/2000 | Chuter |
| 6,033,413 A | 3/2000 | Mikus et al. |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,059,824 A | 5/2000 | Taheri |
| 6,063,092 A | 5/2000 | Shin |
| 6,063,113 A | 5/2000 | Kavteladze et al. |
| 6,068,635 A | 5/2000 | Gianotti |
| 6,070,589 A | 6/2000 | Keith et al. |
| 6,074,398 A | 6/2000 | Leschinsky |
| 6,077,295 A | 6/2000 | Limon et al. |
| 6,077,296 A | 6/2000 | Shokoohi et al. |
| 6,077,297 A | 6/2000 | Robinson et al. |
| 6,080,191 A | 6/2000 | Summers |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,005 A | 8/2000 | Botich et al. |
| 6,096,027 A | 8/2000 | Layne |
| 6,106,548 A | 8/2000 | Reubin et al. |
| 6,110,180 A | 8/2000 | Foreman et al. |
| 6,113,607 A | 9/2000 | Lau et al. |
| 6,117,142 A | 9/2000 | Goodson et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,132,458 A | 10/2000 | Stachle et al. |
| 6,139,532 A | 10/2000 | Howell et al. |
| 6,143,016 A | 11/2000 | Bleam et al. |
| 6,146,389 A | 11/2000 | Geitz |
| 6,146,415 A | 11/2000 | Fitz |
| 6,149,680 A | 11/2000 | Shelso et al. |
| 6,152,944 A | 11/2000 | Holman et al. |
| 6,159,195 A | 12/2000 | Ha et al. |
| 6,159,198 A | 12/2000 | Gardeski et al. |
| 6,162,237 A | 12/2000 | Chan |
| 6,165,195 A | 12/2000 | Wilson et al. |
| 6,165,214 A | 12/2000 | Lazarus |
| 6,168,610 B1 | 1/2001 | Marin et al. |
| 6,171,281 B1 | 1/2001 | Zhang |
| 6,174,327 B1 | 1/2001 | Mertens et al. |
| 6,183,443 B1 | 2/2001 | Kratoska et al. |
| 6,183,481 B1 | 2/2001 | Lee et al. |
| 6,183,509 B1 | 2/2001 | Dibie |
| 6,187,036 B1 | 2/2001 | Shaolian et al. |
| 6,187,037 B1 | 2/2001 | Satz |
| 6,192,944 B1 | 2/2001 | Greenhalgh |
| 6,193,726 B1 | 2/2001 | Vanney |
| 6,197,007 B1 | 3/2001 | Thorne et al. |
| 6,197,016 B1 | 3/2001 | Fourkas et al. |
| 6,197,049 B1 | 3/2001 | Shaolian et al. |
| 6,203,735 B1 | 3/2001 | Edwin et al. |
| 6,210,429 B1 | 4/2001 | Vardi et al. |
| 6,214,038 B1 | 4/2001 | Piplani et al. |
| 6,221,081 B1 | 4/2001 | Mikus et al. |
| 6,221,090 B1 | 4/2001 | Wilson |
| 6,221,098 B1 | 4/2001 | Wilson |
| 6,221,102 B1 | 4/2001 | Baker et al. |
| 6,224,627 B1 | 5/2001 | Armstrong et al. |
| 6,228,062 B1 | 5/2001 | Howell et al. |
| 6,231,563 B1 | 5/2001 | White et al. |
| 6,238,410 B1 | 5/2001 | Vrba et al. |
| 6,254,609 B1 | 7/2001 | Vrba et al. |
| 6,254,628 B1 | 7/2001 | Wallace et al. |
| 6,258,099 B1 | 7/2001 | Mareiro et al. |
| 6,261,316 B1 | 7/2001 | Shaolian et al. |
| 6,264,682 B1 | 7/2001 | Wilson et al. |
| 6,273,895 B1 | 8/2001 | Pinchuk et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,283,991 B1 | 9/2001 | Cox et al. |
| 6,287,329 B1 | 9/2001 | Duering et al. |
| 6,299,634 B1 | 10/2001 | Bergeron |
| 6,302,893 B1 | 10/2001 | Limon et al. |
| 6,312,406 B1 | 11/2001 | Jayaraman |
| 6,331,184 B1 | 12/2001 | Abrams |
| 6,331,190 B1 | 12/2001 | Shokoohi et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,557 B1 | 3/2002 | Gittings et al. |
| 6,361,559 B1 | 3/2002 | Houser et al. |
| 6,361,637 B2 | 3/2002 | Martin et al. |
| 6,379,365 B1 | 4/2002 | Diaz |
| 6,380,457 B1 | 4/2002 | Yurek et al. |
| 6,383,213 B2 | 5/2002 | Wilson et al. |
| 6,387,120 B2 | 5/2002 | Wilson et al. |
| 6,395,017 B1 | 5/2002 | Dwyer et al. |
| 6,395,018 B1 | 5/2002 | Castaneda |

(56) References Cited

U.S. PATENT DOCUMENTS

| | | |
|---|---|---|
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,529 B1 | 7/2002 | Holman et al. |
| 6,416,542 B1 | 7/2002 | Marcade et al. |
| 6,428,567 B2 | 8/2002 | Wilson et al. |
| 6,432,130 B1 | 8/2002 | Hanson |
| 6,432,131 B1 | 8/2002 | Ravenscroft |
| 6,432,134 B1 | 8/2002 | Anson et al. |
| 6,440,161 B1 | 8/2002 | Madrid et al. |
| 6,447,540 B1 | 9/2002 | Fontaine et al. |
| 6,451,043 B1 | 9/2002 | McInnes et al. |
| 6,464,721 B1 | 10/2002 | Marcade et al. |
| 6,468,298 B1 | 10/2002 | Pelton |
| 6,475,166 B1 | 11/2002 | Escano |
| 6,475,170 B1 | 11/2002 | Doron et al. |
| 6,478,777 B1 | 11/2002 | Honeck et al. |
| 6,482,211 B1 | 11/2002 | Choi |
| 6,485,513 B1 | 11/2002 | Fan |
| 6,491,719 B1 | 12/2002 | Fogrty et al. |
| 6,500,202 B1 | 12/2002 | Shaolian et al. |
| 6,508,790 B1 | 1/2003 | Lawrence |
| 6,508,833 B2 | 1/2003 | Pavcnick et al. |
| 6,508,835 B1 | 1/2003 | Shaolian et al. |
| 6,508,836 B1 | 1/2003 | Wilson et al. |
| 6,511,325 B1 | 1/2003 | Lalka et al. |
| 6,514,281 B1 | 2/2003 | Blaeser et al. |
| 6,517,522 B1 | 2/2003 | Bell et al. |
| 6,517,569 B2 | 2/2003 | Mikus et al. |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,554,848 B2 | 4/2003 | Boylan et al. |
| 6,558,396 B1 | 5/2003 | Inoue |
| 6,562,063 B1 | 5/2003 | Euteneurer et al. |
| 6,565,596 B1 | 5/2003 | White et al. |
| 6,565,597 B1 | 5/2003 | Fearnot et al. |
| 6,569,192 B1 | 5/2003 | Foreman et al. |
| RE38,146 E | 6/2003 | Palmaz et al. |
| 6,572,643 B1 | 6/2003 | Gharibadeh |
| 6,572,645 B2 | 6/2003 | Leonhardt |
| 6,576,005 B1 | 6/2003 | Geitz |
| 6,576,006 B2 | 6/2003 | Limon et al. |
| 6,576,009 B2 | 6/2003 | Ryan et al. |
| 6,579,312 B2 | 6/2003 | Wilson et al. |
| 6,582,390 B1 | 6/2003 | Sanderson |
| 6,582,394 B1 | 6/2003 | Reiss et al. |
| 6,582,459 B1 | 6/2003 | Lau et al. |
| 6,582,460 B1 | 6/2003 | Cryer |
| 6,585,758 B1 | 7/2003 | Chouinard et al. |
| 6,589,213 B2 | 7/2003 | Reydel |
| 6,589,251 B2 | 7/2003 | Yee et al. |
| 6,589,262 B1 | 7/2003 | Honebrink et al. |
| 6,592,548 B2 | 7/2003 | Jayaraman |
| 6,592,581 B2 | 7/2003 | Bowe |
| 6,592,614 B2 | 7/2003 | Lenker et al. |
| 6,592,615 B1 | 7/2003 | Marcade et al. |
| 6,599,315 B2 | 7/2003 | Wilson |
| 6,602,280 B2 | 8/2003 | Chobotov |
| 6,607,551 B1 | 8/2003 | Sullivan et al. |
| 6,607,552 B1 | 8/2003 | Hanson |
| 6,613,073 B1 | 9/2003 | White et al. |
| 6,613,075 B1 | 9/2003 | Healy et al. |
| 6,616,675 B1 | 9/2003 | Evard et al. |
| 6,620,191 B1 | 9/2003 | Svensson |
| 6,641,564 B1 | 11/2003 | Kraus |
| 6,652,492 B1 | 11/2003 | Bell et al. |
| 6,652,579 B1 | 11/2003 | Cox et al. |
| 6,656,213 B2 | 12/2003 | Solem |
| 6,660,030 B2 | 12/2003 | Shaolian et al. |
| 6,663,665 B2 | 12/2003 | Shaolian et al. |
| 6,669,716 B1 | 12/2003 | Gilson et al. |
| 6,669,718 B2 | 12/2003 | Besselink |
| 6,669,719 B2 | 12/2003 | Wallace et al. |
| 6,673,102 B1 | 1/2004 | Vonesh et al. |
| 6,676,666 B2 | 1/2004 | Vrba et al. |
| 6,676,667 B2 | 1/2004 | Mareiro et al. |
| 6,689,157 B2 | 2/2004 | Madrid et al. |
| 6,699,274 B2 | 3/2004 | Stinson |
| 6,699,275 B1 | 3/2004 | Knudson et al. |
| 6,702,843 B1 | 3/2004 | Brown et al. |
| 6,702,845 B1 | 3/2004 | Cully et al. |
| 6,722,705 B2 | 4/2004 | Korkor |
| 6,723,075 B2 | 4/2004 | Davey et al. |
| 6,733,523 B2 | 5/2004 | Shaolian et al. |
| 6,743,210 B2 | 6/2004 | Hart et al. |
| 6,749,627 B2 | 6/2004 | Thompson et al. |
| 6,752,819 B1 | 6/2004 | Brady et al. |
| 6,755,855 B2 | 6/2004 | Yurek et al. |
| 6,761,733 B2 | 7/2004 | Chobotov et al. |
| 6,767,359 B2 | 7/2004 | Weadock |
| 6,790,224 B2 | 9/2004 | Gerberding |
| 6,792,979 B2 | 9/2004 | Konya et al. |
| 6,800,065 B2 | 10/2004 | Duane et al. |
| 6,808,509 B1 | 10/2004 | Davey |
| 6,808,520 B1 | 10/2004 | Fourkas et al. |
| 6,814,752 B1 | 11/2004 | Chuter |
| 6,818,014 B2 | 11/2004 | Brown et al. |
| 6,821,292 B2 | 11/2004 | Pazienza et al. |
| 6,827,726 B2 | 12/2004 | Parodi |
| 6,840,950 B2 | 1/2005 | Standford et al. |
| 6,846,316 B2 | 1/2005 | Abrams |
| 6,849,084 B2 | 2/2005 | Rabkin et al. |
| 6,849,086 B2 | 2/2005 | Cragg |
| 6,858,038 B2 | 2/2005 | Heuser |
| 6,866,669 B2 | 3/2005 | Buzzard et al. |
| 6,872,193 B2 | 3/2005 | Shaw et al. |
| 6,875,229 B2 | 4/2005 | Wilson et al. |
| 6,878,158 B2 | 4/2005 | Shin et al. |
| 6,887,249 B1 | 5/2005 | Houser et al. |
| 6,887,251 B1 | 5/2005 | Suval |
| 6,887,256 B2 | 5/2005 | Gilson et al. |
| 6,896,699 B2 | 5/2005 | Wilson et al. |
| 6,899,727 B2 | 5/2005 | Armstrong et al. |
| 6,899,728 B1 | 5/2005 | Phillips et al. |
| 6,908,477 B2 | 6/2005 | McGuckin |
| 6,911,039 B2 | 6/2005 | Shiu et al. |
| 6,918,925 B2 | 7/2005 | Tehrani |
| 6,923,829 B2 | 8/2005 | Boyle et al. |
| 6,926,732 B2 | 8/2005 | Derus et al. |
| 6,929,661 B2 | 8/2005 | Bolduc et al. |
| 6,932,837 B2 | 8/2005 | Amplatz et al. |
| 6,939,352 B2 | 9/2005 | Buzzard et al. |
| 6,939,368 B2 | 9/2005 | Simso |
| 6,939,370 B2 | 9/2005 | Hartley et al. |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,945,990 B2 | 9/2005 | Greenean |
| 6,953,475 B2 | 10/2005 | Shaolian et al. |
| 6,955,679 B1 | 10/2005 | Hendricksen et al. |
| 6,955,688 B2 | 10/2005 | Wilson et al. |
| 6,960,217 B2 | 11/2005 | Bolduc |
| 6,962,602 B2 | 11/2005 | Vardi |
| 6,981,982 B2 | 1/2006 | Armstrong et al. |
| 6,984,244 B2 | 1/2006 | Perez et al. |
| 6,991,639 B2 | 1/2006 | Holman et al. |
| 6,994,722 B2 | 2/2006 | DiCarlo |
| 7,004,926 B2 | 2/2006 | Navia et al. |
| 7,004,964 B2 | 2/2006 | Thompson |
| 7,004,967 B2 | 2/2006 | Chouinard et al. |
| 7,014,653 B2 | 3/2006 | Ouriel et al. |
| 7,022,133 B2 | 4/2006 | Yee et al. |
| 7,025,773 B2 | 4/2006 | Gittings et al. |
| 7,025,779 B2 | 4/2006 | Elliott |
| 7,029,496 B2 | 4/2006 | Rakos et al. |

(56) References Cited

U.S. PATENT DOCUMENTS

| | | |
|---|---|---|
| 7,052,511 B2 | 5/2006 | Weldon et al. |
| 7,056,323 B2 | 6/2006 | Mareiro et al. |
| 7,074,236 B2 | 7/2006 | Rabkin et al. |
| 7,096,554 B2 | 8/2006 | Austin et al. |
| 7,101,390 B2 | 9/2006 | Nelson |
| 7,105,016 B2 | 9/2006 | Shiu et al. |
| 7,105,017 B2 | 9/2006 | Kerr |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,127,789 B2 | 10/2006 | Stinson |
| 7,137,993 B2 | 11/2006 | Acosta et al. |
| 7,144,422 B1 | 12/2006 | Rao |
| 7,160,318 B2 | 1/2007 | Greenberg et al. |
| 7,162,302 B2 | 1/2007 | Wang et al. |
| 7,163,715 B1 | 1/2007 | Kramer |
| 7,172,577 B2 | 2/2007 | Mangano et al. |
| 7,175,651 B2 | 2/2007 | Kerr |
| 7,175,652 B2 | 2/2007 | Cook et al. |
| 7,175,657 B2 | 2/2007 | Khan et al. |
| 7,189,256 B2 | 3/2007 | Smith |
| 7,189,257 B2 | 3/2007 | Schmitt et al. |
| 7,201,770 B2 | 4/2007 | Johnson et al. |
| 7,229,472 B2 | 6/2007 | DePalma et al. |
| 7,235,095 B2 | 6/2007 | Haverkost et al. |
| 7,241,308 B2 | 7/2007 | Andreas et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,285,130 B2 | 10/2007 | Austin |
| 7,297,156 B2 | 11/2007 | Nelson |
| 7,300,454 B2 | 11/2007 | Park et al. |
| 7,314,481 B2 | 1/2008 | Karpiel |
| 7,314,483 B2 | 1/2008 | Landau et al. |
| 7,316,708 B2 | 1/2008 | Gordon et al. |
| 7,320,703 B2 | 1/2008 | DiMatteo et al. |
| 7,331,980 B2 | 2/2008 | Dubrul et al. |
| 7,367,980 B2 | 5/2008 | Kida et al. |
| 7,381,216 B2 | 6/2008 | Buzzard et al. |
| 7,402,168 B2 | 7/2008 | Acosta et al. |
| 7,407,509 B2 | 8/2008 | Greenberg et al. |
| 7,413,560 B2 | 8/2008 | Chong et al. |
| 7,419,501 B2 | 9/2008 | Chiu et al. |
| 7,425,219 B2 | 9/2008 | Quadri et al. |
| 7,435,253 B1 | 10/2008 | Hartley et al. |
| 7,473,271 B2 | 1/2009 | Gunderson |
| 7,476,244 B2 | 1/2009 | Buzzard et al. |
| 7,481,805 B2 | 1/2009 | Magnusson |
| 7,491,230 B2 | 2/2009 | Holman et al. |
| 7,520,895 B2 | 4/2009 | Douglas et al. |
| 7,526,849 B2 | 5/2009 | Serrano |
| 7,537,606 B2 | 5/2009 | Hartley |
| 7,553,319 B2 | 6/2009 | Bagaoisan et al. |
| 7,553,324 B2 | 6/2009 | Andreas et al. |
| 7,572,289 B2 | 8/2009 | Sisken et al. |
| 7,578,838 B2 | 8/2009 | Melsheimer |
| 7,578,841 B2 | 8/2009 | Yadin et al. |
| 7,591,832 B2 | 9/2009 | Eversull et al. |
| 7,618,398 B2 | 11/2009 | Holman et al. |
| 7,632,299 B2 | 12/2009 | Weber |
| 7,635,382 B2 | 12/2009 | Pryor |
| 7,635,383 B2 | 12/2009 | Gumm |
| 7,637,932 B2 | 12/2009 | Bolduc et al. |
| 7,641,684 B2 | 1/2010 | Hilaire et al. |
| 7,651,519 B2 | 1/2010 | Dittman |
| 7,666,219 B2 | 2/2010 | Rasmussen et al. |
| 7,674,284 B2 | 3/2010 | Melsheimer |
| 7,678,141 B2 | 3/2010 | Greenan et al. |
| 7,691,135 B2 | 4/2010 | Shaolian et al. |
| 7,691,139 B2 | 4/2010 | Baker et al. |
| 7,695,508 B2 | 4/2010 | Van Der Leest et al. |
| 7,699,885 B2 | 4/2010 | Leonhardt et al. |
| 7,717,923 B2 | 5/2010 | Kennedy, II et al. |
| 7,722,657 B2 | 5/2010 | Hartley |
| 7,736,337 B2 | 6/2010 | Diep et al. |
| 7,736,383 B2 | 6/2010 | Bressler et al. |
| 7,736,384 B2 | 6/2010 | Bressler et al. |
| 7,753,951 B2 | 7/2010 | Shaked et al. |
| 7,758,625 B2 | 7/2010 | Wu et al. |
| 7,763,063 B2 | 7/2010 | Arbefeuille et al. |
| 7,766,952 B2 | 8/2010 | Horan et al. |
| 7,771,463 B2 | 8/2010 | Ton et al. |
| 7,785,340 B2 | 8/2010 | Heidner et al. |
| 7,785,361 B2 | 8/2010 | Nikolchev et al. |
| 7,794,473 B2 | 9/2010 | Tessmer et al. |
| 7,799,266 B2 | 9/2010 | Parker et al. |
| 7,833,259 B2 | 11/2010 | Boatman |
| 7,837,724 B2 | 11/2010 | Keeble et al. |
| 7,842,066 B2 | 11/2010 | Gilson et al. |
| 7,846,135 B2 | 12/2010 | Runfola |
| 7,867,267 B2 | 1/2011 | Sullivan et al. |
| 7,867,270 B2 | 1/2011 | Hartley |
| 7,871,419 B2 | 1/2011 | Devellian et al. |
| 7,871,430 B2 | 1/2011 | Pavcnik et al. |
| 7,879,081 B2 | 2/2011 | DeMatteo et al. |
| 7,883,537 B2 | 2/2011 | Grayzel et al. |
| 7,922,755 B2 | 4/2011 | Acosta et al. |
| 7,935,140 B2 | 5/2011 | Griffin |
| 7,942,924 B1 | 5/2011 | Perez et al. |
| 8,002,814 B2 | 8/2011 | Kennedy, II et al. |
| 8,021,420 B2 | 9/2011 | Dolan |
| 8,025,692 B2 | 9/2011 | Feeser |
| 8,034,100 B2 | 10/2011 | Shaolian et al. |
| 8,062,344 B2 | 11/2011 | Dorn et al. |
| 8,075,607 B2 | 12/2011 | Melsheimer |
| 8,075,608 B2 | 12/2011 | Gordon et al. |
| 8,092,508 B2 | 1/2012 | Leynov et al. |
| 8,167,892 B2 | 5/2012 | Feller, III et al. |
| 8,182,522 B2 | 5/2012 | Sarac et al. |
| 8,216,295 B2 | 7/2012 | Benjamin et al. |
| 8,236,040 B2 | 8/2012 | Mayberry et al. |
| 8,523,931 B2 | 9/2013 | Mayberry et al. |
| 8,808,350 B2 | 8/2014 | Schreck et al. |
| 8,821,564 B2 | 9/2014 | Schreck et al. |
| 8,844,430 B2 | 9/2014 | Mastropasqua et al. |
| 8,945,202 B2 | 2/2015 | Mayberry et al. |
| 2001/0049547 A1 | 12/2001 | Moore |
| 2002/0019660 A1 | 2/2002 | Gianotti |
| 2002/0049412 A1 | 4/2002 | Madrid et al. |
| 2002/0072712 A1* | 6/2002 | Nool ............... A61M 25/0136 604/167.01 |
| 2002/0120322 A1 | 8/2002 | Thompson et al. |
| 2002/0123786 A1 | 9/2002 | Gittings et al. |
| 2002/0156516 A1 | 10/2002 | Vardi |
| 2002/0193806 A1 | 12/2002 | Moenning et al. |
| 2003/0004560 A1 | 1/2003 | Chobotov et al. |
| 2003/0004561 A1 | 1/2003 | Bigus et al. |
| 2003/0065386 A1 | 4/2003 | Weadock |
| 2003/0074043 A1 | 4/2003 | Thompson |
| 2003/0083730 A1 | 5/2003 | Stinson |
| 2003/0097169 A1 | 5/2003 | Brucker et al. |
| 2003/0125751 A1 | 7/2003 | Griffin et al. |
| 2003/0167060 A1 | 9/2003 | Buzzard et al. |
| 2003/0225445 A1 | 12/2003 | Derus et al. |
| 2003/0236565 A1 | 12/2003 | DiMatteo et al. |
| 2004/0006380 A1 | 1/2004 | Buck et al. |
| 2004/0015150 A1 | 1/2004 | Zadno-Azizi |
| 2004/0039400 A1 | 2/2004 | Schmieding et al. |
| 2004/0044395 A1 | 3/2004 | Nelson |
| 2004/0098084 A1 | 5/2004 | Hartley et al. |
| 2004/0111095 A1 | 6/2004 | Gordon et al. |
| 2004/0167618 A1 | 8/2004 | Shaolian et al. |
| 2004/0176832 A1 | 9/2004 | Hartley et al. |
| 2004/0193180 A1 | 9/2004 | Buzzard et al. |
| 2004/0210239 A1 | 10/2004 | Nash et al. |
| 2004/0215312 A1 | 10/2004 | Andreas |
| 2004/0225344 A1 | 11/2004 | Hoffa et al. |
| 2004/0230286 A1 | 11/2004 | Moore et al. |
| 2005/0021123 A1 | 1/2005 | Dorn et al. |
| 2005/0027305 A1 | 2/2005 | Shiu et al. |
| 2005/0027345 A1 | 2/2005 | Horan et al. |

(56) References Cited

U.S. PATENT DOCUMENTS

| | | |
|---|---|---|
| 2005/0033403 A1 | 2/2005 | Ward et al. |
| 2005/0038494 A1 | 2/2005 | Eidenschink |
| 2005/0038495 A1 | 2/2005 | Greenan |
| 2005/0049607 A1 | 3/2005 | Hart et al. |
| 2005/0049667 A1 | 3/2005 | Arbefeuille et al. |
| 2005/0049672 A1 | 3/2005 | Murphy |
| 2005/0049678 A1 | 3/2005 | Cocks et al. |
| 2005/0058327 A1 | 3/2005 | Pieper |
| 2005/0059994 A1 | 3/2005 | Walak et al. |
| 2005/0060016 A1 | 3/2005 | Wu et al. |
| 2005/0060025 A1 | 3/2005 | Mackiewicz et al. |
| 2005/0080476 A1 | 4/2005 | Gunderson et al. |
| 2005/0113693 A1 | 5/2005 | Smith et al. |
| 2005/0113905 A1 | 5/2005 | Greenberg et al. |
| 2005/0119731 A1 | 6/2005 | Brucker et al. |
| 2005/0121043 A1 | 6/2005 | Abrams |
| 2005/0121120 A1 | 6/2005 | Van Dijk et al. |
| 2005/0125002 A1 | 6/2005 | Baran et al. |
| 2005/0154441 A1 | 7/2005 | Schaeffer et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0171599 A1 | 8/2005 | White |
| 2005/0216043 A1 | 9/2005 | Blatter et al. |
| 2005/0222668 A1 | 10/2005 | Schaeffer et al. |
| 2005/0240153 A1 | 10/2005 | Opie |
| 2005/0240255 A1 | 10/2005 | Schaeffer |
| 2005/0240258 A1 | 10/2005 | Bolduc et al. |
| 2005/0240260 A1 | 10/2005 | Bolduc |
| 2005/0246008 A1 | 11/2005 | Hogendijk |
| 2005/0273150 A1 | 12/2005 | Howell et al. |
| 2005/0288772 A1 | 12/2005 | Douglas |
| 2006/0018948 A1 | 1/2006 | Guire et al. |
| 2006/0052750 A1 | 3/2006 | Lenker et al. |
| 2006/0095050 A1 | 5/2006 | Hartley et al. |
| 2006/0100658 A1 | 5/2006 | Obana et al. |
| 2006/0129223 A1 | 6/2006 | Jabbour et al. |
| 2006/0142838 A1 | 6/2006 | Molaei et al. |
| 2006/0161244 A1 | 7/2006 | Sequin |
| 2006/0184226 A1 | 8/2006 | Austin |
| 2006/0184237 A1 | 8/2006 | Weber et al. |
| 2006/0200223 A1 | 9/2006 | Andreas et al. |
| 2006/0212107 A1 | 9/2006 | Case et al. |
| 2006/0217794 A1 | 9/2006 | Ruiz et al. |
| 2006/0229561 A1 | 10/2006 | Huszar |
| 2006/0233990 A1 | 10/2006 | Humphrey et al. |
| 2006/0233991 A1 | 10/2006 | Humphrey et al. |
| 2006/0264801 A1 | 11/2006 | Bolling et al. |
| 2006/0265045 A1 | 11/2006 | Shiu et al. |
| 2006/0276872 A1 | 12/2006 | Arbefeuille et al. |
| 2007/0005001 A1 | 1/2007 | Rowe et al. |
| 2007/0010867 A1 | 1/2007 | Carter et al. |
| 2007/0027522 A1 | 2/2007 | Chang et al. |
| 2007/0027526 A1 | 2/2007 | Demetriades et al. |
| 2007/0043421 A1 | 2/2007 | Mangiardi et al. |
| 2007/0043430 A1 | 2/2007 | Stinson |
| 2007/0049906 A1 | 3/2007 | Magnusson |
| 2007/0050006 A1* | 3/2007 | Lavelle ............ A61M 27/008 623/1.11 |
| 2007/0055339 A1 | 3/2007 | George et al. |
| 2007/0055360 A1 | 3/2007 | Hanson et al. |
| 2007/0060914 A1 | 3/2007 | Magnusson |
| 2007/0112420 A1 | 5/2007 | LaDuca |
| 2007/0118207 A1 | 5/2007 | Amplatz et al. |
| 2007/0118208 A1 | 5/2007 | Kerr |
| 2007/0156224 A1 | 7/2007 | Cioanta et al. |
| 2007/0167955 A1 | 7/2007 | Arnault De La Menardiere et al. |
| 2007/0168014 A1 | 7/2007 | Jimenez |
| 2007/0191775 A1 | 8/2007 | Diep et al. |
| 2007/0191927 A1 | 8/2007 | Bowe et al. |
| 2007/0203571 A1 | 8/2007 | Kaplan et al. |
| 2007/0213805 A1 | 9/2007 | Schaeffer et al. |
| 2007/0225659 A1 | 9/2007 | Melsheimer |
| 2007/0225797 A1 | 9/2007 | Krivoruhko |
| 2007/0239254 A1 | 10/2007 | Chia et al. |
| 2007/0244540 A1 | 10/2007 | Pryor |
| 2007/0260301 A1 | 11/2007 | Chuter et al. |
| 2007/0260302 A1 | 11/2007 | Igaki |
| 2007/0282302 A1 | 12/2007 | Wachsman et al. |
| 2007/0299497 A1 | 12/2007 | Shaolian et al. |
| 2007/0299499 A1 | 12/2007 | Hartley |
| 2008/0015681 A1 | 1/2008 | Wilson |
| 2008/0027528 A1 | 1/2008 | Jagger et al. |
| 2008/0033354 A1 | 2/2008 | Hartley et al. |
| 2008/0046005 A1 | 2/2008 | Lenker et al. |
| 2008/0071343 A1 | 3/2008 | Mayberry et al. |
| 2008/0082052 A1 | 4/2008 | Schnell et al. |
| 2008/0082154 A1 | 4/2008 | Tseng et al. |
| 2008/0086191 A1 | 4/2008 | Valencia |
| 2008/0109065 A1 | 5/2008 | Bowe |
| 2008/0125849 A1 | 5/2008 | Burpee et al. |
| 2008/0140003 A1 | 6/2008 | Bei et al. |
| 2008/0172042 A1 | 7/2008 | House |
| 2008/0172122 A1 | 7/2008 | Mayberry et al. |
| 2008/0208319 A1 | 8/2008 | Rabkin et al. |
| 2008/0269867 A1 | 10/2008 | Johnson |
| 2008/0294230 A1 | 11/2008 | Parker |
| 2009/0012602 A1 | 1/2009 | Quadri |
| 2009/0030495 A1 | 1/2009 | Koch |
| 2009/0099638 A1 | 4/2009 | Grewe |
| 2009/0105798 A1 | 4/2009 | Koch |
| 2009/0105806 A1 | 4/2009 | Benjamin et al. |
| 2009/0138065 A1 | 5/2009 | Zhang et al. |
| 2009/0192586 A1 | 7/2009 | Tabor et al. |
| 2009/0216315 A1 | 8/2009 | Schreck et al. |
| 2009/0254165 A1 | 10/2009 | Tabor et al. |
| 2009/0259298 A1 | 10/2009 | Mayberry et al. |
| 2009/0266238 A1 | 10/2009 | Mastropasqua et al. |
| 2009/0276028 A1 | 11/2009 | Bailey et al. |
| 2010/0004730 A1 | 1/2010 | Benjamin et al. |
| 2010/0030318 A1 | 2/2010 | Berra |
| 2010/0057185 A1 | 3/2010 | Melsheimer et al. |
| 2010/0094393 A1 | 4/2010 | Cordeiro et al. |
| 2010/0114290 A1 | 5/2010 | Rasmussen et al. |
| 2010/0160863 A1 | 6/2010 | Heuser |
| 2010/0168674 A1 | 7/2010 | Shaw et al. |
| 2010/0168834 A1 | 7/2010 | Ryan et al. |
| 2010/0179635 A1 | 7/2010 | Dittman |
| 2010/0179636 A1 | 7/2010 | Mayberry et al. |
| 2010/0179638 A1 | 7/2010 | Shaolian et al. |
| 2010/0262157 A1 | 10/2010 | Silver et al. |
| 2010/0268234 A1 | 10/2010 | Aho et al. |
| 2010/0274270 A1 | 10/2010 | Patel et al. |
| 2010/0274340 A1 | 10/2010 | Hartley et al. |
| 2011/0009945 A1 | 1/2011 | Parker et al. |
| 2011/0015718 A1 | 1/2011 | Schreck |
| 2011/0015728 A1 | 1/2011 | Jimenez et al. |
| 2011/0046712 A1 | 2/2011 | Melsheimer et al. |
| 2011/0054586 A1 | 3/2011 | Mayberry et al. |
| 2011/0054587 A1 | 3/2011 | Mayberry et al. |
| 2011/0054594 A1 | 3/2011 | Mayberry et al. |
| 2011/0121023 A1 | 5/2011 | Milan |
| 2011/0178588 A1 | 7/2011 | Haselby |
| 2011/0218607 A1 | 9/2011 | Arbefeuille et al. |
| 2011/0218617 A1 | 9/2011 | Nguyen et al. |
| 2011/0224742 A1 | 9/2011 | Weisel et al. |
| 2011/0224772 A1 | 9/2011 | Mayberry et al. |
| 2011/0224782 A1 | 9/2011 | Douglas et al. |
| 2011/0251664 A1 | 10/2011 | Acosta De Acevedo |
| 2011/0257718 A1 | 10/2011 | Argentine |
| 2011/0270371 A1 | 11/2011 | Argentine |
| 2011/0282425 A1 | 11/2011 | Dwork |
| 2011/0313503 A1 | 12/2011 | Berra et al. |
| 2012/0029610 A1 | 2/2012 | Shaolian et al. |
| 2012/0109279 A1 | 5/2012 | Mayberry et al. |
| 2012/0123517 A1 | 5/2012 | Ouellette et al. |
| 2012/0226341 A1 | 9/2012 | Schreck et al. |
| 2013/0184805 A1 | 7/2013 | Sawada |
| 2014/0358214 A1 | 12/2014 | Schreck et al. |

FOREIGN PATENT DOCUMENTS

| | | |
|---|---|---|
| CN | 105232195 A | 1/2016 |
| DE | 295 21 548 U1 | 2/1995 |

(56) References Cited

FOREIGN PATENT DOCUMENTS

| | | |
|---|---|---|
| DE | 295 21 776 U1 | 2/1995 |
| DE | 100 17 147 | 10/2001 |
| EP | 0 177 330 | 6/1991 |
| EP | 0 564 373 | 10/1993 |
| EP | 0 596 145 | 5/1994 |
| EP | 0 621 015 | 10/1994 |
| EP | 0 659 389 | 6/1995 |
| EP | 0 688 545 | 12/1995 |
| EP | 0 689 806 | 1/1996 |
| EP | 0 712 614 | 5/1996 |
| EP | 0 732 088 | 9/1996 |
| EP | 0 740 928 A1 | 11/1996 |
| EP | 0 740 928 B1 | 11/1996 |
| EP | 0 747 020 | 12/1996 |
| EP | 0 775 470 | 5/1997 |
| EP | 0 782 841 | 7/1997 |
| EP | 0 783 873 | 7/1997 |
| EP | 0 783 874 | 7/1997 |
| EP | 0 875 262 | 11/1997 |
| EP | 0 880 938 | 12/1998 |
| EP | 0 880 948 | 12/1998 |
| EP | 0 904 745 | 3/1999 |
| EP | 0 974 314 | 1/2000 |
| EP | 0 732 088 | 4/2000 |
| EP | 1 358 903 | 11/2003 |
| EP | 1 508 313 | 2/2005 |
| EP | 2 680 915 | 1/2014 |
| ES | 1 038 606 | 7/1998 |
| GB | 1 193 759 | 6/1970 |
| JP | 04-25755 | 1/1992 |
| JP | H05-81257 | 11/1993 |
| JP | 06-23057 | 2/1994 |
| JP | 30-09638 | 4/1994 |
| JP | 08-052165 | 2/1996 |
| JP | 08-336597 | 12/1996 |
| JP | 09-164209 | 6/1997 |
| JP | 9-511160 | 11/1997 |
| JP | 2000-500047 | 1/2000 |
| JP | 2004-130068 | 4/2004 |
| JP | 2005-516742 | 6/2005 |
| JP | 2009-525139 | 7/2009 |
| JP | 2010-536418 | 12/2010 |
| JP | 2013-508080 | 3/2013 |
| WO | WO 90/14054 | 11/1990 |
| WO | WO 93/13825 | 7/1993 |
| WO | WO 94/24961 | 11/1994 |
| WO | WO 95/21592 | 8/1995 |
| WO | WO 96/14808 | 5/1996 |
| WO | WO 96/34580 | 11/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/17911 | 5/1997 |
| WO | WO 97/19652 | 6/1997 |
| WO | WO 97/26936 | 7/1997 |
| WO | WO 97/033532 | 9/1997 |
| WO | WO 97/045072 | 12/1997 |
| WO | WO 98/02100 | 1/1998 |
| WO | WO 98/53761 | 12/1998 |
| WO | WO 99/029262 | 6/1999 |
| WO | WO 99/44536 | 9/1999 |
| WO | WO 99/47077 | 9/1999 |
| WO | WO 99/58084 | 11/1999 |
| WO | WO 00/78248 | 12/2000 |
| WO | WO 02/36179 | 5/2002 |
| WO | WO 02/39888 | 5/2002 |
| WO | WO 02/060345 | 8/2002 |
| WO | WO 03/068302 | 8/2003 |
| WO | WO 05/037076 | 4/2005 |
| WO | WO 05/037141 | 4/2005 |
| WO | WO 05/067819 | 7/2005 |
| WO | WO 06/071915 | 7/2006 |
| WO | WO 06/117321 | 11/2006 |
| WO | WO 07/027830 | 3/2007 |
| WO | WO 07/092276 | 8/2007 |
| WO | WO 09/023221 | 2/2009 |
| WO | WO 11/049808 | 4/2011 |
| WO | WO 12/118901 | 9/2012 |

OTHER PUBLICATIONS

US 6,413,270 B1, 07/2002, Thornton et al. (withdrawn)
U.S. Appl. No. 12/769,506, filed Apr. 28, 2010, Mayberry et al.
U.S. Appl. No. 12/769,581, filed Apr. 28, 2010, Mayberry et al.
U.S. Appl. No. 12/695,546, filed Apr. 28, 2010, Mayberry et al.
International Partial Search Report re PCT/US2009/049316, dated Oct. 19, 2009.
International Search Report and Written Opinion re PCT/US2009/049316, dated Dec. 11, 2009.
European Office Action dated Jul. 11, 2013, from application No. 12178965.5.
European Office Action dated Jun. 28, 2011, from application No. 09774381.9.
European Office Action dated Jun. 30, 2014, from application No. 12178965.5.
European Office Action dated Mar. 9, 2016, from application No. 12178965.5.
Final Office Action dated Apr. 28, 2016, from U.S. Appl. No. 13/544,426.
Final Office Action dated Aug. 16, 2013, from U.S. Appl. No. 13/544,426.
Non-final Office Action dated Feb. 26, 2013, from U.S. Appl. No. 13/544,426.
Non-final Office Action dated Jan. 27, 2014, from U.S. Appl. No. 13/544,426.
Non-final office Action dated Oct. 13, 2011, from U.S. Appl. No. 12/496,446.
Non-final Office Action dated Sep. 11, 2015, from U.S. Appl. No. 13/544,426.
Non-final Office Action dated Sep. 26, 2016, from U.S. Appl. No. 13/544,426.
Notice of Allowance dated Feb. 13, 2017, from U.S. Appl. No. 13/544,426.
Notice of Allowance dated Mar. 7, 2012, from U.S. Appl. No. 12/496,446.
Notice of Allowance dated May 17, 2017, from U.S. Appl. No. 13/544,426.
Notice of Reasons for Refusal dated Jul. 10, 2012, from Japanese application No. 2011-516829.

* cited by examiner

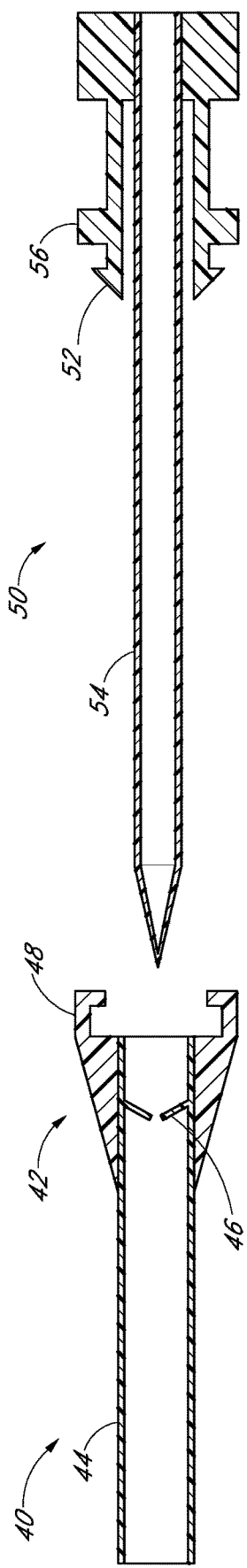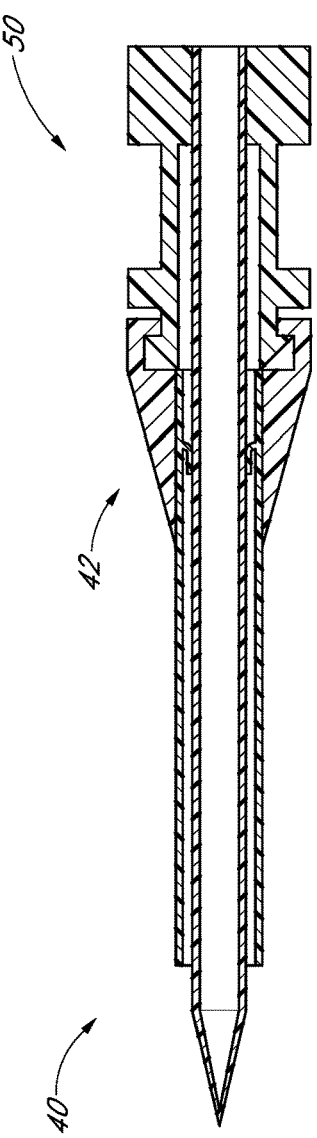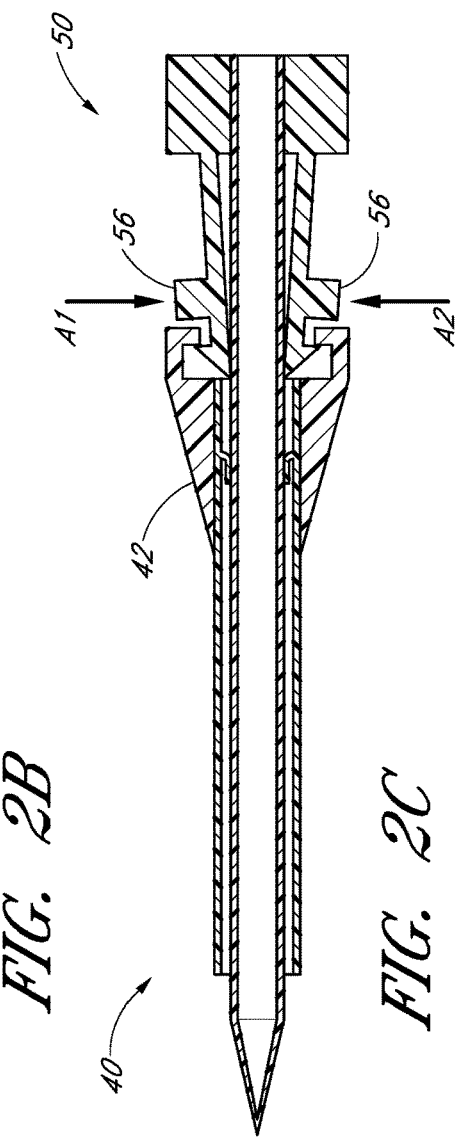
FIG. 2A
FIG. 2B
FIG. 2C

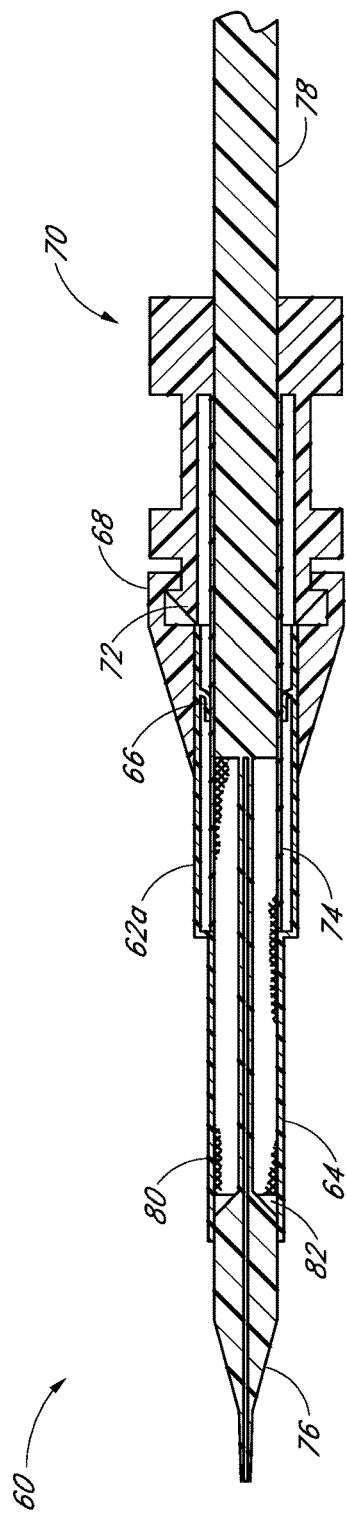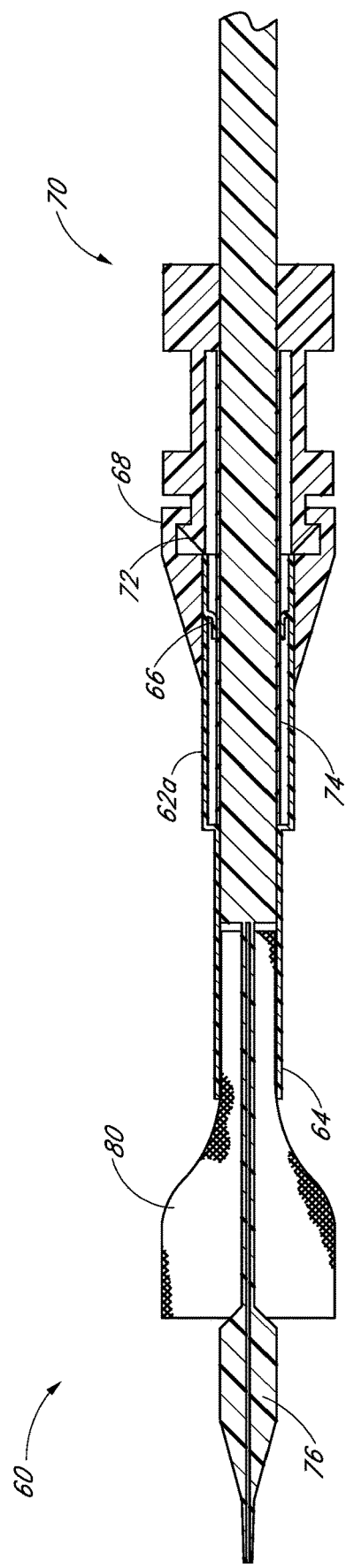

CATHETER SYSTEM AND METHODS OF USING SAME

PRIORITY CLAIM AND INCORPORATION BY REFERENCE

This application is a continuation of U.S. patent application Ser. No. 13/544,426, filed Jul. 9, 2012, which is a continuation of U.S. patent application Ser. No. 12/496,446, now U.S. Pat. No. 8,216,295, filed on Jul. 1, 2009 (entitled "CATHETER SYSTEM AND METHODS OF USING SAME"), which claims the benefit under 35 U.S.C. § 119 of U.S. Provisional Patent Application No. 61/077,429, filed Jul. 1, 2008 (entitled "CATHETER SYSTEM AND METHODS OF USING SAME"), and U.S. Provisional Patent Application No. 61/184,742, filed Jun. 5, 2009 (entitled "CATHETER SYSTEM AND METHODS OF USING SAME"), the entirety of each of which is hereby incorporated by reference as if fully set forth herein.

BACKGROUND OF THE INVENTION

Technical Field

The present invention relates to catheter systems, in particular, catheter systems having an introducer.

Description of the Related Art

Introducers or introducer sheaths are used for minimal invasive placement of catheters into blood vessels. They typically consist of a tubing that is inserted into the blood vessel and a seal or valve at the proximal end of the tubing which is positioned outside of the body. The seal provides a hemostasis seal against blood loss. Catheters used for diagnostic or therapeutic means are typically passed through the introducer into the blood vessel. The introducer sheath thus provides continuous access for catheters, protects the inner wall of the blood vessel against damage during catheter insertion, and provides a hemostasis seal against blood loss.

There are situations in which the catheters require substantial maneuvering within the blood vessel. For example, placement of a stent or stent graft may require the delivery catheter to be positioned precisely axially as well as possible rotationally into a specific location within the blood vessel. In addition deployment of the stent may require precise operation of the delivery system within the introducer. In these situations, the operator has to carefully control both the position of the introducer and the delivery system. This sometimes requires assistance by a second operator.

SUMMARY OF THE INVENTION

Some embodiments disclosed herein pertain to a catheter system for the insertion and positioning of diagnostic or therapeutic devices into blood vessels. In some embodiments, the system comprises an introducer or an introducer sheath and at least one catheter. The catheter can be introduced through the introducer into the blood stream. A docking mechanism can engage the proximal end of the introducer with the proximal end of the catheter and can prevent axial movement between the introducer and the catheter.

In some embodiments, a catheter system can comprise an introducer and a catheter, wherein the introducer can comprise a sheath (that can be tubular) and a seal that can be an adjustable hemostasis valve connected to the proximal end of the sheath. The introducer can define a proximal end and a distal end, and the catheter can be configured to engage with the proximal end of the introducer. The introducer and the catheter can be configured such that the catheter can be slidingly received within the introducer. The introducer and the catheter can be configured such that the catheter can removably engage with the introducer such that, when the catheter is engaged with the introducer, the catheter will be axially fixed to the introducer so as to prevent substantial axial movement between the introducer and the catheter and so that the catheter and introducer can be manipulated in an axial direction as a single unit.

Additionally, in some embodiments, the catheter and introducer can be configured such that, when the catheter is engaged with the introducer, an inner core of the catheter can be rotatable relative to the introducer and the introducer sheath. Further, in some embodiments, the catheter can be configured such that the inner core of the catheter can be locked or substantially prevented from rotational movement relative to the outer sheath of the catheter and/or relative to the introducer.

In some embodiments, a method of placement of a catheter into a blood vessel is provided, wherein the catheter is passed through an introducer sheath and the proximal end of the introducer sheath physically engages with, or is removably docked with, the catheter to prevent substantial axial motion between the introducer sheath and the catheter.

Some stents or stent grafts (collectively referred to herein as a stent or stents) may require precise placement in both axial and circumferential direction. For example, stents or stent grafts with fenestrations require accurate placement of the fenestration at the branch vessel. The embodiments of the catheter systems disclosed herein can be configured to allow for the rotation of the delivery catheter and, hence, the stent, relative to the introducer sheath. In tight and calcified vessels there is often considerable friction between the outer sheath of the catheter and the vessel wall. In some of the embodiments disclosed herein, the delivery catheter and introducer can be configured such that the outer sheath of the delivery catheter will not be in direct contact with the vessel wall during the stent delivery procedure. Rather, in some embodiments, some or all of the length of the outer sheath of the delivery catheter can be contained within the introducer sheath, and the introducer sheath can be in direct contact with the vessel wall. This can considerably reduce the force required to rotate the delivery system relative to the patient's vessel. Accordingly, the delivery catheter and the introducer can be configured such that the delivery catheter can be substantially free to rotate within the introducer sheath.

In some embodiments, the friction that can otherwise impede the rotational freedom of the delivery catheter can be further reduced by lining the inner surface of the introducer sheath with a low-friction coating such as PTFE or applying hydrophilic coating to the outer surface of the delivery catheter or the inner surface of the introducer sheath.

Thus, in some embodiments, the introducer sheath can remain rotationally static or still while the deployment catheter is rotated within the introducer sheath. This can protect the delivery catheter and stent from being damaged, torqued, or stressed during the rotational manipulation of the delivery catheter and stent, and also prevent any damage or stress on the vessel wall from the rotation of the delivery catheter or stent.

Additionally, in some embodiments, delivery catheter can be configured to permit a user or medical practitioner to selectively control or prevent the rotational freedom of the delivery catheter and stent relative to the introducer, or the inner core of the delivery catheter and stent relative to the outer sheath of the delivery catheter. For example, in some embodiments, the delivery catheter can comprise a threaded hub supported at the proximal end portion of the delivery catheter configured to selectively constrict or tighten against an outer wall of the inner core of the delivery catheter. By constricting the hub against the inner core, the inner core can be prevented or inhibited from rotating relative to the introducer. By loosening the hub relative to the inner core, the rotational freedom of the inner core or delivery catheter relative to the introducer sheath can be restored.

In some embodiments, the hemostasis valve of the introducer sheath can be opened and closed by rotating the handle of the introducer sheath so as to be adjustable. Active adjustment of the hemostasis valve may be desired to seal against catheters with a wide range of diameters. The docking mechanism can allow the handle of the introducer sheath to be operated (i.e. rotated) while a catheter is inserted in and docked to the introducer sheath. Furthermore, the catheter can be rotationally locked by closing the valve.

Some embodiments are directed to a catheter system that can comprise an introducer comprising a main body, a introducer sheath projecting from the main body, and a first seal (which can be a rubber seal, an interference or close tolerance fit between adjacent components, an adjustable hemostasis valve, or any other suitable sealing component or feature) supported within the introducer, and a catheter comprising a main body, a outer sheath projecting from the main body, a second seal (which can be a rubber seal, an interference or close tolerance fit between adjacent components, an adjustable hemostasis valve, or any other suitable sealing component or feature) supported within the catheter, and an inner core that is advanceable through the main body, the second seal, and the outer sheath. The first seal can be configured to at least inhibit a flow of blood through the introducer when the catheter is engaged with the introducer. The second seal can be configured to at least inhibit a flow of blood through the catheter. The introducer sheath can be configured to axially receive at least the inner core therethrough. In some embodiments, the introducer can be configured to be selectively engageable with the catheter so that the catheter can be selectively and removably linked with the introducer in the axial direction such that, when the introducer and the catheter are linked, the axial movement of either of the introducer and the catheter will cause the simultaneous and equal axial movement of the other of the introducer and the catheter. In some embodiments, the catheter system can be configured such that, when the introducer and the catheter are linked, the catheter is rotatable relative to the introducer.

Some embodiments are directed to a catheter system that can comprise an introducer comprising a main body and an introducer sheath projecting from the main body, a catheter comprising a main body, a outer sheath projecting from the main body, and an inner core that is advanceable through the main body and the outer sheath. In some embodiments, the inner core can be configured to axially support a stent such that the stent can be advanced through the outer sheath by advancing the inner core through the outer sheath. The outer sheath can be configured to radially restrain the stent so that no additional radial restraint is required. In some embodiments, the outer sheath can be configured to radially restrain the stent in addition to other forms of restraint. The introducer sheath can be configured to axially receive at least the inner core therein. In some embodiments, the catheter system can be configured such that the outer sheath of the catheter does not advance into the introducer sheath when the catheter is fully axially advanced into the introducer. In some embodiments, the introducer sheath can be configured to directly radially restrain the stent while the stent is positioned within the introducer sheath.

Therefore, in some embodiments, the outer sheath of the catheter and the introducer sheath can be configured to provide a lumen having a generally uniform cross-sectional size through the catheter system through which the endoluminal prosthesis can be advanced. In some embodiments, the lumen through the catheter system through which the endoluminal prosthesis can be advanced can be substantially continuous, so that the endoluminal prosthesis can be advanced through the catheter system without the prosthesis being obstructed by or snagging on any components or features of the catheter system as it is being advanced. In some embodiments, the lumen can be substantially continuous but have short gaps on the order of approximately 1 mm to approximately 3 mm in the lumen such as, without limitation, adjacent to the distal end of the outer sheath of the catheter and/or adjacent to the proximal end of the introducer sheath. Further, in some embodiments, one or more surfaces of other components comprising the catheter or the introducer in addition to the outer sheath and the introducer sheath, such as without limitation the main body of the introducer, can form portions of the lumen through the catheter system.

Some embodiments are directed to a method of deploying a stent in a blood vessel, comprising positioning an introducer within a patient's blood vessel so as to advance an introducer sheath of the introducer into the patient's blood vessel, the introducer having a proximal end portion and a distal end portion, advancing an outer sheath of a catheter into the introducer so that an end portion of the outer sheath of the catheter is positioned approximately adjacent to the proximal end portion of the introducer sheath and such that no portion of the outer sheath overlaps the introducer sheath, the catheter further comprising an inner core that is axially moveable within the outer sheath, axially supporting a stent with the inner core, axially advancing the inner core and the stent through the outer sheath of the catheter, through the introducer sheath, and past the distal end of the introducer sheath, and deploying the stent in the blood vessel.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 2A is a schematic representation of another embodiment of a catheter system comprising a docking arrangement to physically engage a catheter with an introducer sheath.

FIG. 2B is a schematic representation of the embodiment of the catheter system shown in FIG. 2A, showing the catheter engaged with the introducer sheath.

FIG. 2C is a schematic representation of the embodiment of the catheter system shown in FIG. 2A, showing a mechanism for disengaging the catheter from the introducer sheath.

FIG. 3C is a schematic representation of the embodiment of the catheter system shown in FIG. 3A, illustrating the axial insertion of an embodiment of a stent into the tubular sheath of the embodiment of the introducer sheath shown in FIG. 3A.

FIG. 3D is a schematic representation of the embodiment of the catheter system shown in FIG. 3A, illustrating the embodiment of the stent being deployed after the tubular sheath of the embodiment of the introducer sheath shown in FIG. 3A has been retracted from the stent.

DETAILED DESCRIPTION OF THE PREFERRED EMBODIMENTS

The following detailed description is now directed to certain specific embodiments of the disclosure. In this description, reference is made to the figures wherein like parts are designated with like numerals throughout the description and the drawings. Described below are various embodiments of a catheter system that can comprise an introducer sheath and a docking arrangement. In some embodiments, the catheter systems disclosed herein can be used in diagnostic or therapeutic procedures such as, but not limited to, endoluminal vascular prosthesis deployment procedures.

Figure 1A:
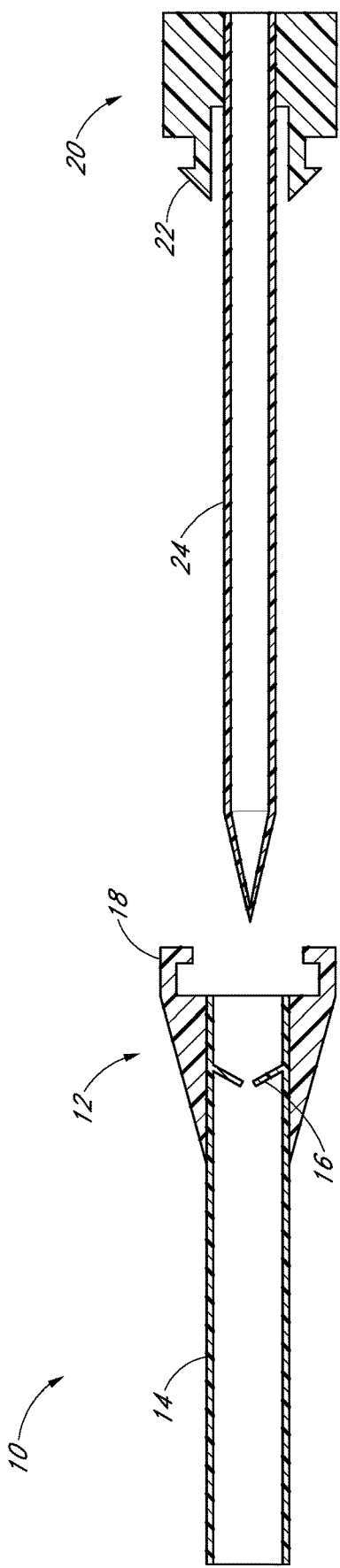
FIG. 1A is a schematic representation of an embodiment of a catheter system comprising a docking arrangement to physically engage a catheter with an introducer sheath.
Figure 1B:
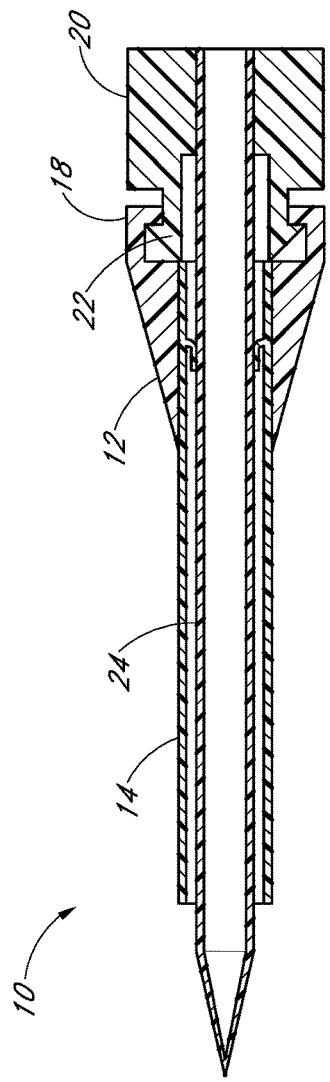
FIG. 1B is a schematic representation of the embodiment of the catheter system shown in FIG. 1A, showing the catheter engaged with the introducer sheath.

FIG. 1A is a schematic representation of an embodiment of a catheter system 10 comprising a docking arrangement configured to physically engage a catheter 20 with an introducer 12. FIG. 1B is a schematic representation of the catheter system 10 shown in FIG. 1A, showing the catheter 20 engaged with the introducer 12. In some embodiments, the catheter 20 or any catheter disclosed herein can be a diagnostic or therapeutic catheter, or any other suitable catheter. In some embodiments, the introducer 12 can comprise a tubular sheath 14, a seal 16, and a female docking mechanism 18. The first seal 16 can be a rubber seal, an interference or close tolerance fit between adjacent components, an adjustable hemostasis valve, or any other suitable sealing component or feature.

In some embodiments, the catheter 20 can have a shaft 24 and a male docking mechanism 22. In some embodiments, as illustrated in FIG. 1B, the catheter 20 can be inserted into the introducer 12 and the female docking mechanism 18 can be engaged with the male docking mechanism 22. In some embodiments, the docking mechanism can prevent the introducer 12 and the catheter 20 from moving axially with respect to each other when the docking mechanism is engaged. Additionally, in some embodiments, the catheter system 10 can be configured so that the catheter 20 can rotate within the introducer 12, even when the catheter 20 is docked with the introducer 12.

As mentioned, the introducer 12 can comprise a tubular introducer sheath 14 and a seal 16 (which, again, can be a rubber seal, an interference or close tolerance fit, an adjustable hemostasis valve, or any other suitable sealing component or feature) connected to the proximal end of the introducer sheath 14. In some embodiments, the overall design of the sheath 14 and seal 16 may be similar to the design of commercially available introducers, or any other introducers presently known or later developed. The catheter 20 can have an outside dimensional profile that is sized and/or configured to pass through the introducer sheath 14. As discussed above, in some embodiments, the proximal end of the catheter 20 and the proximal end of the introducer sheath 14 can be configured to permanently or removably engage with each other, and to allow for the rotation of the catheter 20 within the introducer sheath 14 while substantially limiting the axial movement of the catheter 20 with respect to the introducer sheath 14.

In some embodiments, after engagement of the catheter and introducer, the combined system can be operated by a single operator. As mentioned, the catheter system 10 can be configured so that the catheter 20 can substantially freely rotate within the introducer sheath 14, which can allow for precise rotational positioning of the catheter within the introducer. After completion of the procedure, the catheter 20 can be disengaged from the introducer 12 so that the catheter 20 can be removed from the patient's body. Additionally, the introducer 12 can be repositioned for a second intervention and a second catheter can be inserted and engaged with the introducer 12 for additional procedures.

FIG. 2A is a schematic representation of an embodiment of a catheter system 40 comprising a docking arrangement to physically engage a catheter 50 with an introducer 42. FIG. 2B is a schematic representation of the embodiment of the catheter system 40, showing the catheter 50 engaged with the introducer 42. FIG. 2C is a schematic representation of the embodiment of the catheter system 40 shown in FIG. 2A, showing a mechanism for disengaging the catheter 50 from the introducer 42.

In some embodiments, the catheter system 40 can have a male docking mechanism 52 and a shaft 54. The introducer 42 can comprise a tubular sheath 44, a seal 46, and a female docking mechanism 48. In particular, FIG. 2C schematically illustrates that the catheter 50 can be disengaged from the male docking mechanism 52 and the introducer 42 by compressing the levers or tabs 56. Accordingly, in the illustrated embodiment, the male docking mechanism 52 can be elongated and can comprise levers 56.

Figure 3A:
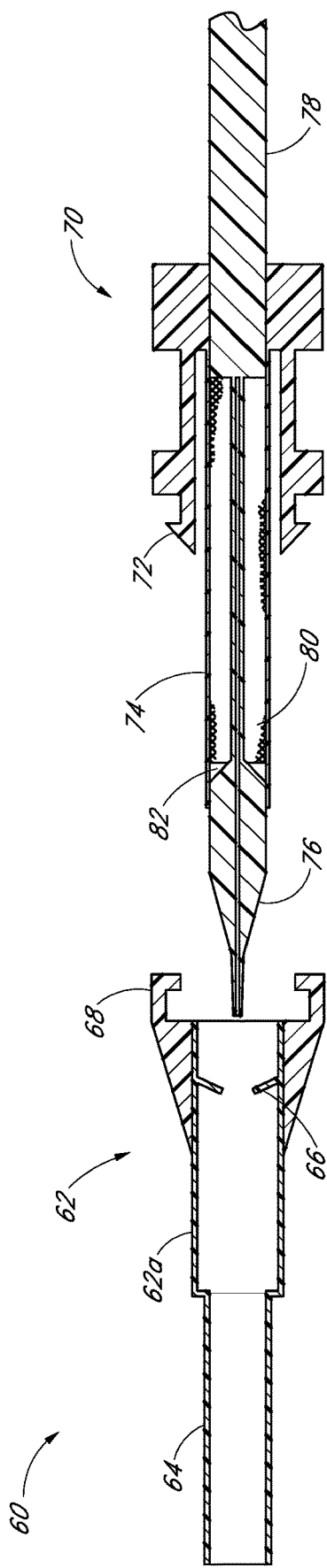
FIG. 3A is a schematic representation of another embodiment of a catheter system comprising a docking arrangement to physically engage a catheter with an introducer sheath, the catheter system being configured to deliver a stent or stent graft into a blood vessel.
Figure 3B:
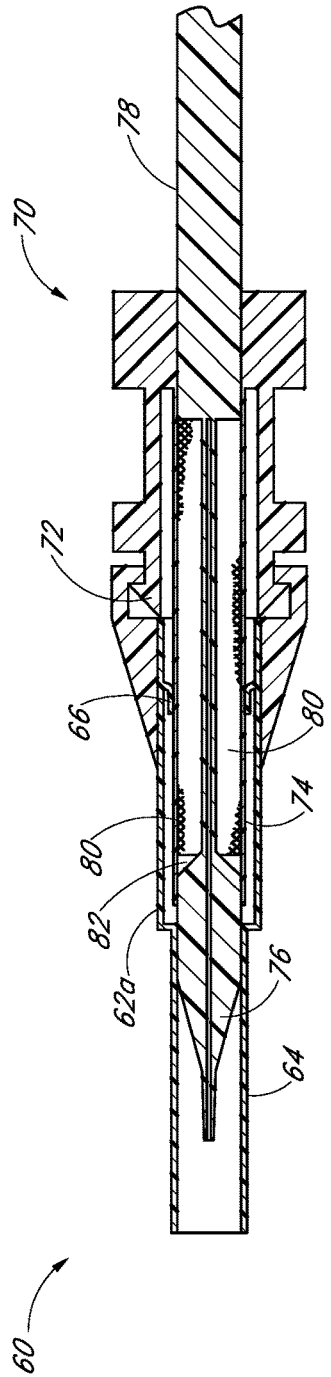
FIG. 3B is a schematic representation of the embodiment of the catheter system shown in FIG. 3A, showing the catheter engaged with the introducer sheath.

FIG. 3A is a schematic representation of another embodiment of a catheter system 60 comprising a docking arrangement to physically engage a catheter 70 with an introducer 62, the catheter system 60 being configured to deliver a stent or stent graft 80 into a blood vessel. FIG. 3B is a schematic representation of the embodiment of the catheter system 60 shown in FIG. 3A, showing the catheter 70 engaged with the introducer 62. FIG. 3C is a schematic representation of the embodiment of the catheter system 60 shown in FIG. 3A, illustrating the axial insertion of an embodiment of a stent or stent graft 80 into the tubular sheath 64 of the embodiment of the introducer 62 shown in FIG. 3A. FIG. 3D is a schematic representation of the embodiment of the catheter system 60 shown in FIG. 3A, illustrating the embodiment of the stent 80 being deployed after the tubular sheath 64 of the embodiment of the introducer 62 shown in FIG. 3A has been retracted from the stent 80.

Self-expanding stent or stents grafts are typically retained in a deployment sheath within the delivery catheter. The deployment sheath can protect the stent or stent graft and the vessel wall from damage during insertion and can retain the stent or stent graft in a collapsed low-profile configuration during delivery. The stent or stent graft can be deployed in the desired position of the blood vessel by removing the deployment sheath and allowing the stent or stent graft to radially expand against the wall of the blood vessel. In order to pass such a delivery catheter into the desired blood vessel, the catheter system can be configured so that the inner diameter of the introducer sheath is larger than the outer diameter of the deployment sheath. Clinicians prefer a low profile of the introducer sheath to minimize damage to the blood vessel and allowing for access into small blood vessels. It can be desired to minimize the profile of the delivery catheter.

Cartridge systems have been developed, in which the stent or stent graft can be transferred from delivery sheath into the introducer sheath and the stent or stent graft can be passed through the introducer sheath to the target location. In such a cartridge system, the introducer sheath effectively acts as a deployment sheath. The transfer eliminates the need of a second sheath and minimizes the profile of the system in the blood vessel. The docking arrangement of the current invention provides a secure engagement of the delivery catheter and the introducer sheath prior to transfer of the stent or stent graft into the introducer sheath. This prevents potential user errors in the transfer and further converts the delivery catheter and introducer sheath into a single-user system.

As illustrated in FIGS. 3A-3D, the catheter system 60 can be used to transfer and deploy a stent or stent graft 80 into a blood vessel (blood vessel not shown). As illustrated therein, the introducer 62 can comprise a tubular sheath 64 that can be inserted into the body of the patient. The proximal end 62a of the introducer 62 can be sized and/or configured to accommodate the deployment sheath 74 of the catheter 70. The introducer sheath can also have a seal 66 (referred to herein as a first seal) and a female docking mechanism 68, similar to any of the embodiments of the seal, hemostasis valve, and/or docking mechanisms described above. The seal 66 can be an annular rubber seal (as illustrated), an interference or close tolerance fit between adjacent components, an adjustable hemostasis valve, or any other suitable sealing component or feature. The stent delivery catheter 70 can comprise an inner core 78, a pocket 82 that can house the collapsed stent 80, a deployment sheath 74 that can retain the collapsed stent 80, and a catheter tip 76.

As illustrated in FIG. 3B, in some embodiments, the catheter 70 can be inserted into the introducer 62 when the docking mechanisms 68 and 72 are engaged. In some embodiments (not illustrated), the deployment sheath 74 of the delivery catheter 70 can be sized and configured to be received within the larger diameter proximal end 62a of the introducer sheath and to extend into the distal tubular sheath 64 of the introducer 62. Alternatively, in some embodiments, the deployment sheath 74 of the delivery catheter 70 can be sized and configured to be received within the larger diameter proximal end 62a of the introducer sheath but not the distal tubular sheath 64 of the introducer 62. In some embodiments, as illustrated in FIGS. 3C and 3D, the deployment sheath 74 and the tubular sheath 64 can be sized and configured such that, when the deployment sheath 74 has advanced through the proximal end 62a of the introducer sheath, the similar size or shape of the distal tubular sheath 64 can prevent the deployment sheath 74 from advancing through the distal tubular sheath 64. In some embodiments, the inner and/or outer diameters of the deployment sheath 74 and the tubular sheath 64 can be substantially the same.

As illustrated in FIG. 3C, in some embodiments, the inner core 78 of the catheter 70 can be pushed distally, thereby transferring the stent 80 from the deployment sheath 74 into the tubular sheath 64 of the introducer 62. The stent 80 can be advanced until the catheter tip 76 reaches the distal end of the tubular sheath 64. In this configuration, the catheter/introducer system effectively becomes a single-unit deployment catheter. Thus, in some embodiments, the tubular sheath 64 can function as a deployment sheath. In some embodiments, the stent 80 can be advanced in a collapsed configuration within the protective introducer 62 to the target location in the blood vessel without increasing the profile of the delivery system. If the delivery catheter were passed through a traditional introducer sheath, the sheath of the introducer would have to be of a larger diameter than the deployment sheath of the delivery catheter in order to accommodate the stent and the deployment sheath.

Figure 4:
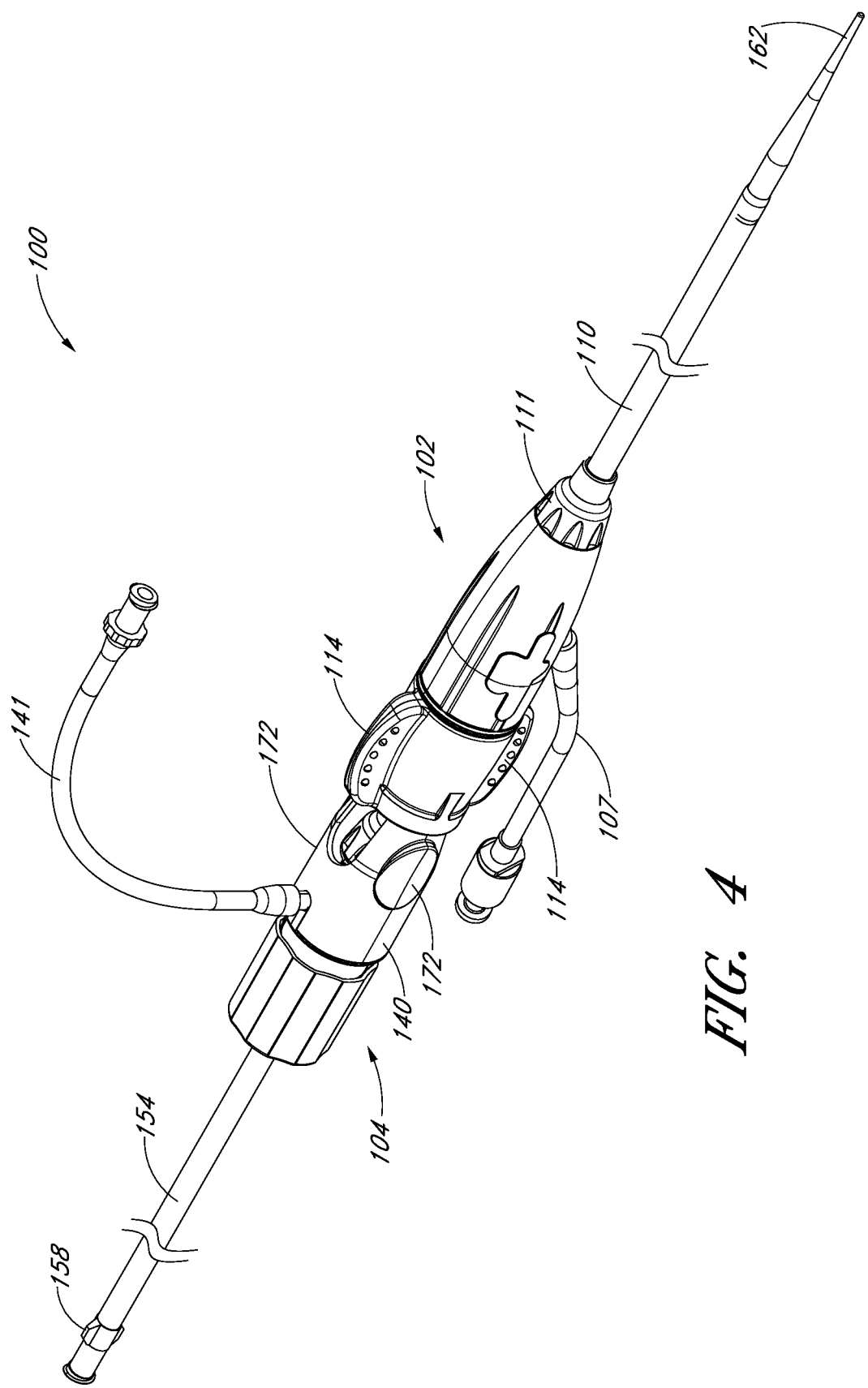
FIG. 4 is a perspective view of an embodiment of a catheter system comprising an embodiment of an introducer and an embodiment of a delivery catheter.

FIG. 4 is a perspective view of another embodiment of a catheter system 100 comprising an introducer catheter 102 (also referred to as an introducer) and a delivery catheter 104. The delivery catheter 104 can be configured for the delivery of an endoluminal prosthesis, or for any other suitable use. Therefore, the embodiments of the catheters and introducers disclosed herein can be configured for any suitable purpose, and the embodiments of the introducers disclosed herein can be configured to receive any suitable catheter design.

Figure 5:
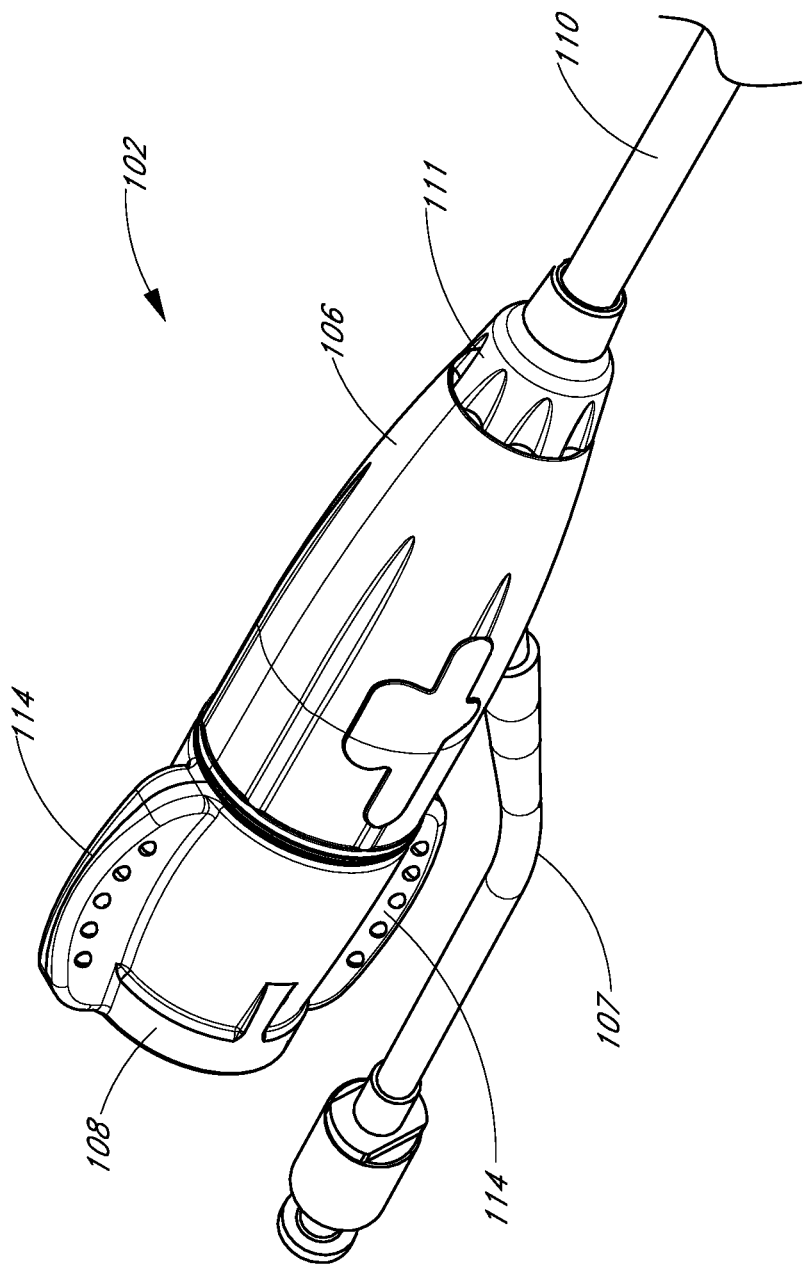
FIG. 5 is a perspective view of the embodiment of the introducer shown in FIG. 4.
Figure 6A:
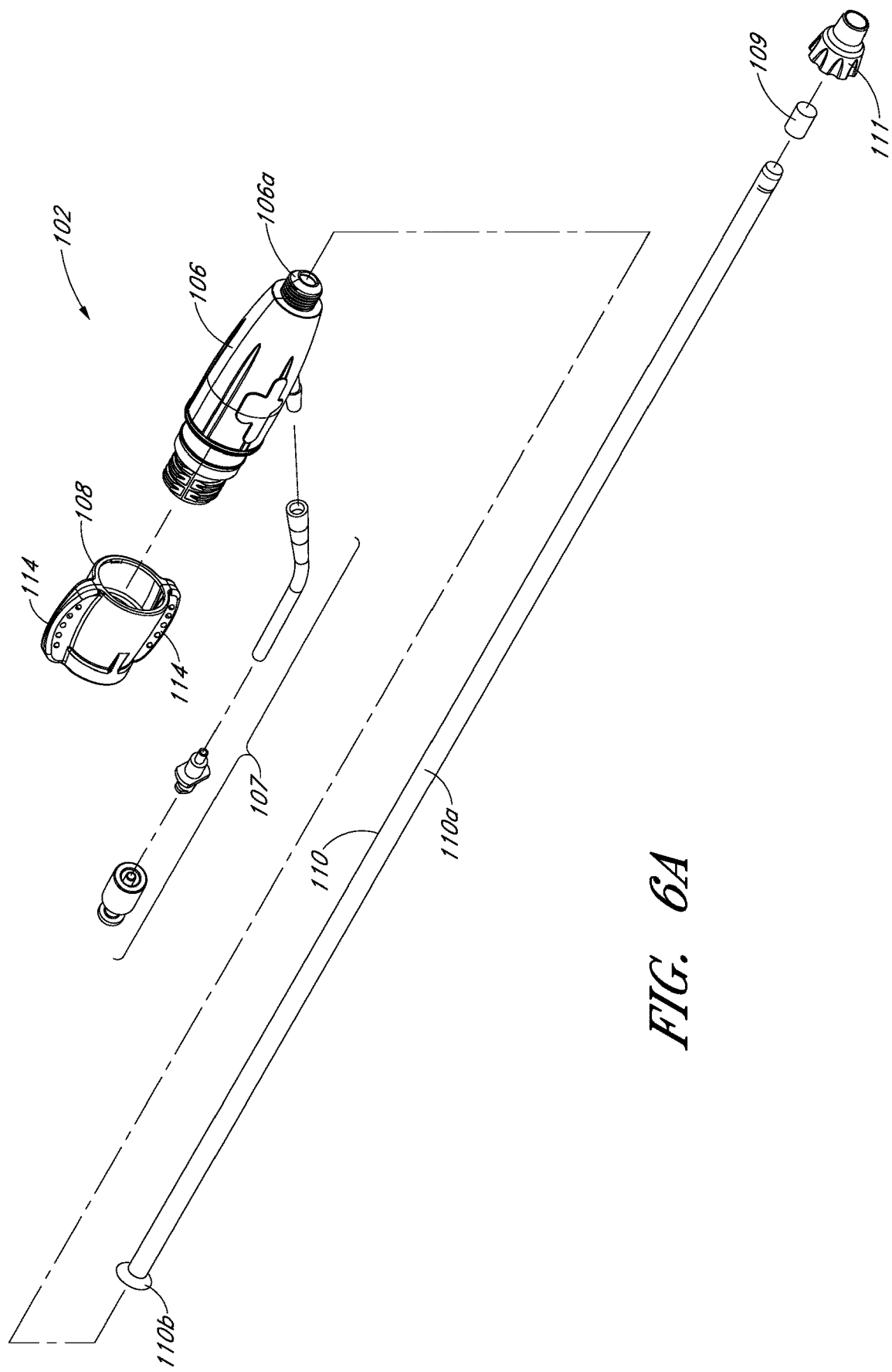
FIG. 6A is a first exploded assembly view of the embodiment of the introducer shown in FIG. 5.
Figure 6B:
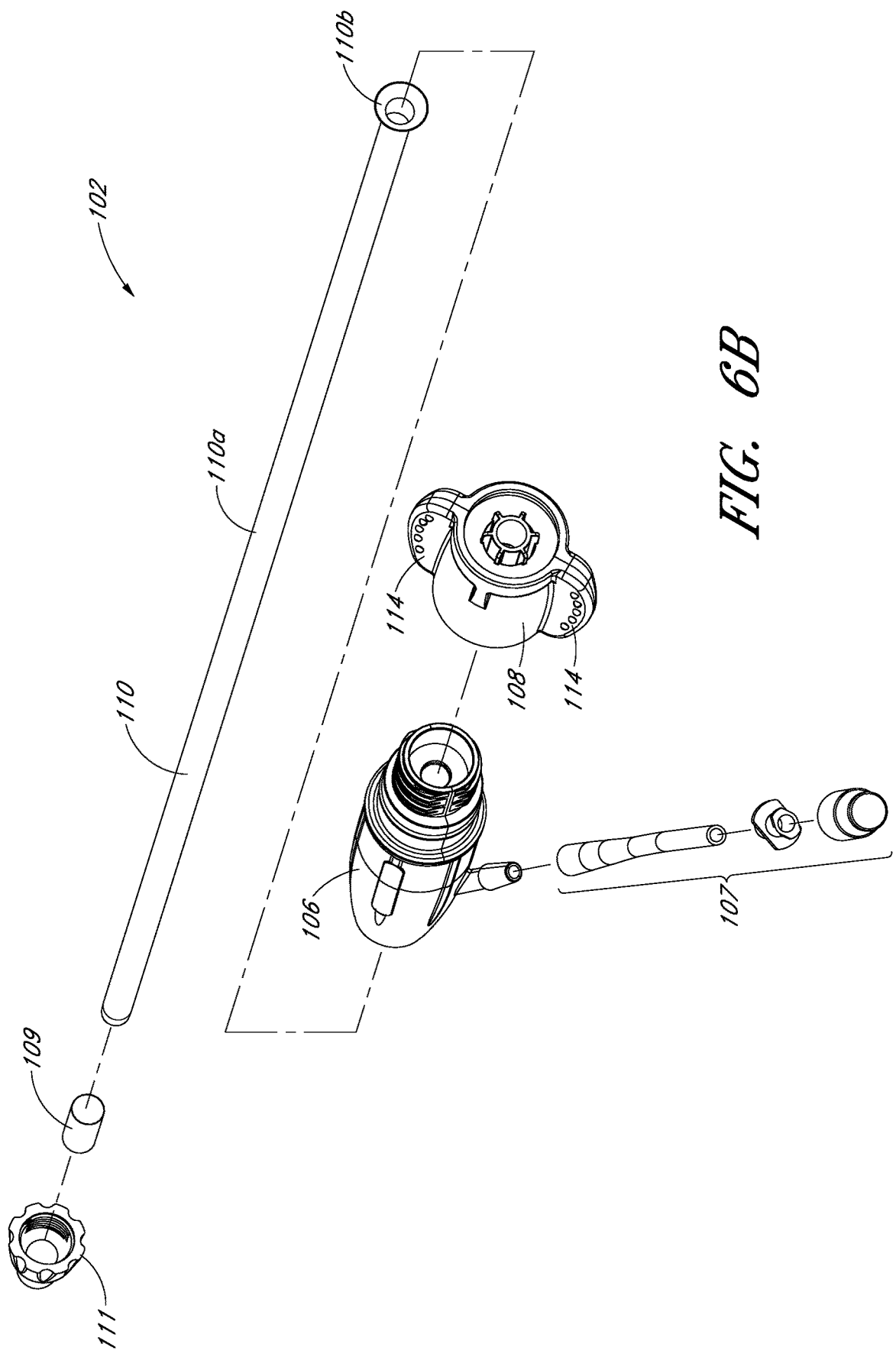
FIG. 6B is a second exploded assembly view of the embodiment of the introducer shown in FIG. 5.

FIG. 5 is a perspective view of the embodiment of the introducer 102 of the embodiment of the catheter system 100 shown in FIG. 4. FIGS. 6A and 6B are a first and a second exploded assembly view of the embodiment of the introducer 102 shown in FIG. 5. With reference to FIGS. 4-6, in some embodiments, the introducer 102 can have a main body 106, a threadably engageable hub portion 108, an introducer sheath 110, and a threaded cap 111 configured to threadably engage with a threaded end portion of the main body 106.

In some embodiments, a first tube 107 can be supported by the main body 106 so as to provide an orifice or access port into the main body 106. The first tube 107 can be used to flush the introducer 102 with saline or other suitable substances at any stage, such as but not limited to prior to the advancement of an endoluminal prosthesis through the introducer 102, or prior to other procedures for which an introducer may be used. The first tube 107 can support any suitable medical connector and/or valve on the distal end thereof.

The introducer sheath 110 can have an elongate portion 110a extending to any predetermined or desired length. As will be discussed in greater detail below, similar to the introducer 12 of the catheter system 10 described above, in some embodiments, the introducer sheath 110 can be configured such that an endoluminal prosthesis that is advanced into the introducer sheath 110 can be constrained or restrained by the introducer sheath 110. In this arrangement, the inside and/or outside diameter of the introducer sheath 110 can be approximately the same as or similar to the inside and/or outside diameter of the outer sheath of a delivery catheter that is engaged with the introducer 102. In some embodiments, the elongate portion 110a can be circular in cross-section (as illustrated), or can define any suitable cross-sectional shape such as without limitation triangular, square, hexagonal, octagonal, or polygonal.

Further, as shown most clearly in FIG. 6A, the introducer sheath 110 can have a flared end portion 110b that can be configured to abut against a fore surface 106a of the main body 106. With reference to FIG. 6A, the elongate portion 110a of the introducer sheath 110 can pass through an opening formed in the cap 111 so that the flared portion 110b of the introducer sheath 110 can be engaged with and/or overlap an inside surface of the cap 111. In this configuration, the cap 111 supporting the introducer sheath 110 can be threadedly engaged with the main body 106 so that the introducer sheath 110 can be supported by the main body 106.

Additionally, with reference to FIGS. 6A and 6B, a tubular support or spacer 109 can be inserted over the elongate portion 110a of the introducer sheath 110 and positioned approximately adjacent to the flared portion 110b. The tubular spacer 109 can improve the fit and, hence, the seal between the outside surface of the introducer sheath 110 and the cap 111. The tubular spacer 109 can also provide additional support to the introducer sheath 110.

Figure 7:
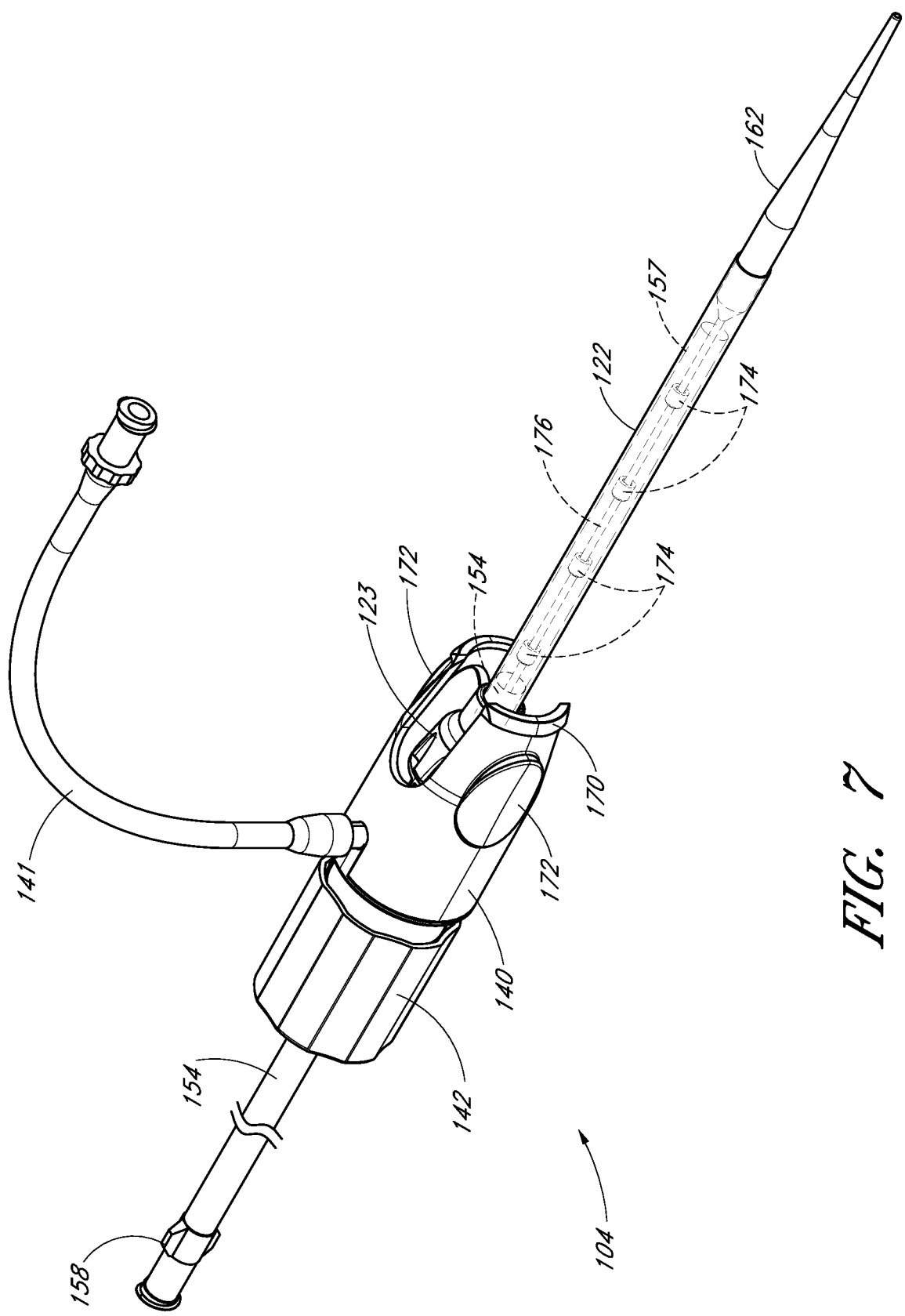
FIG. 7 is a perspective view of the embodiment of the delivery catheter shown in FIG. 4.
Figure 8A:
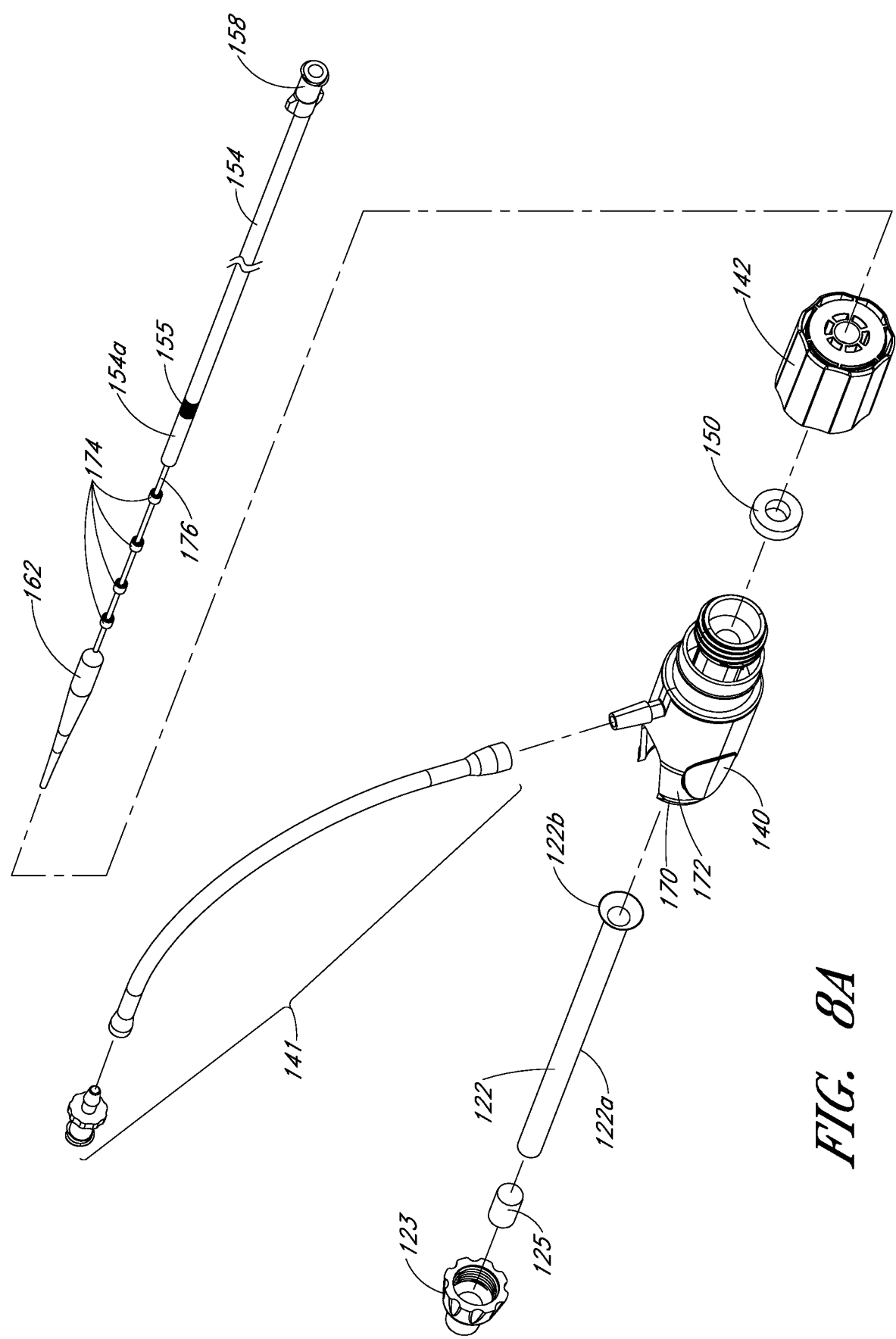
FIG. 8A is a first exploded assembly view of the embodiment of the delivery catheter shown in FIG. 7.
Figure 8B:
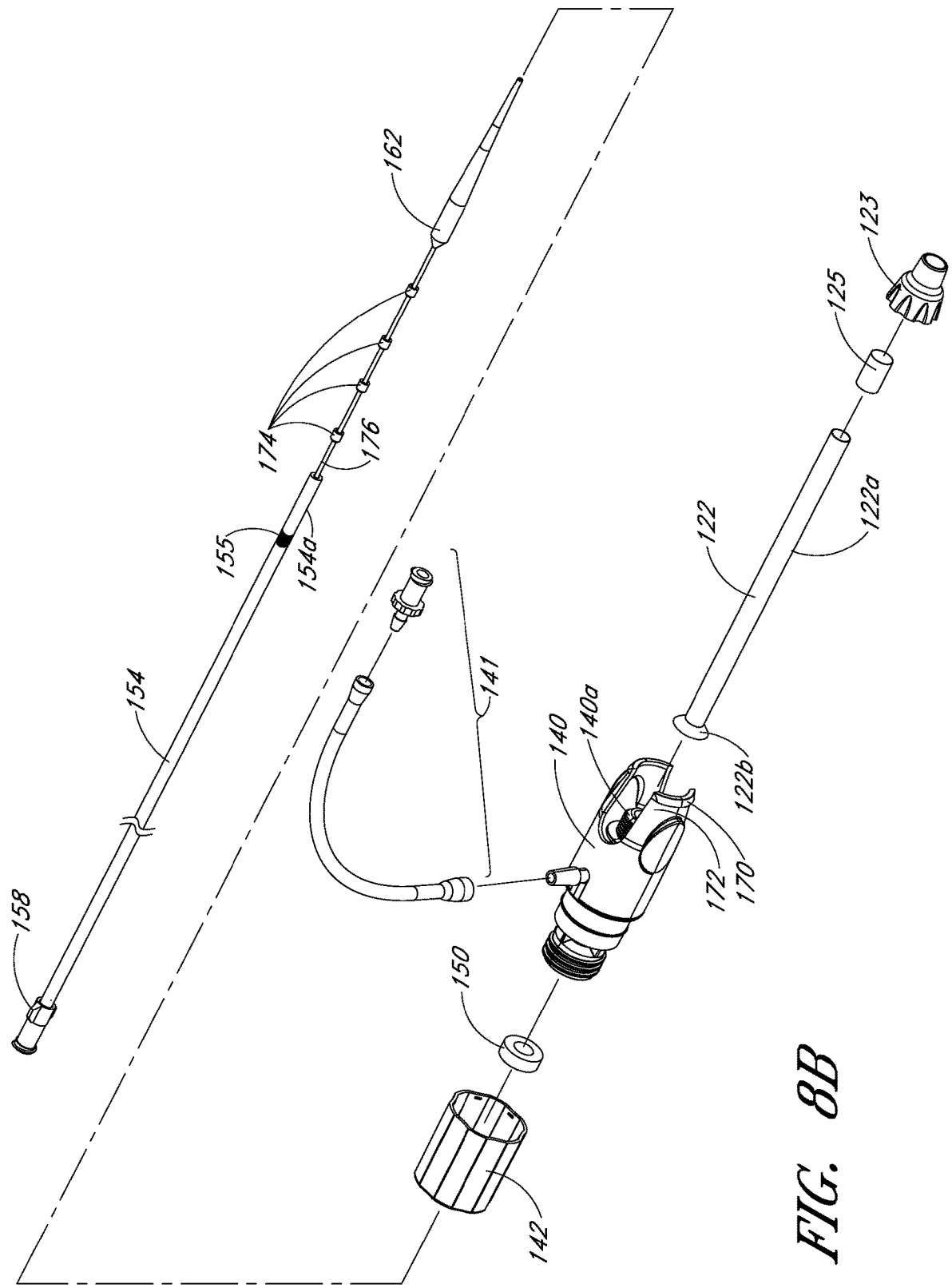
FIG. 8B is a second exploded assembly view of the embodiment of the delivery catheter shown in FIG. 7.
Figure 9:
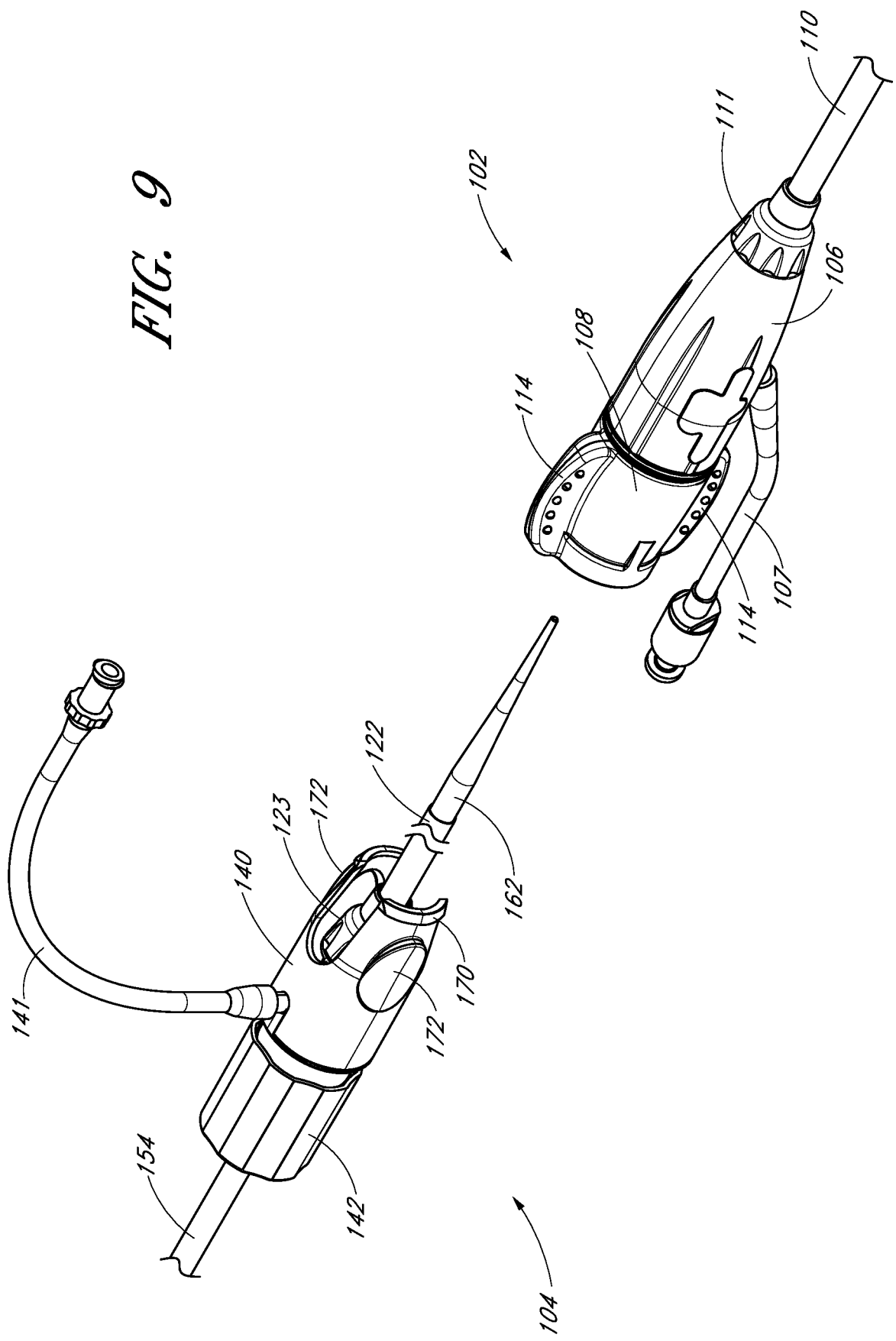
FIG. 9 is a perspective view of the embodiment of the catheter system shown in FIG. 4, showing the delivery catheter before the docking mechanism of the delivery catheter has been engaged with the docking mechanism of the introducer.
Figure 10:
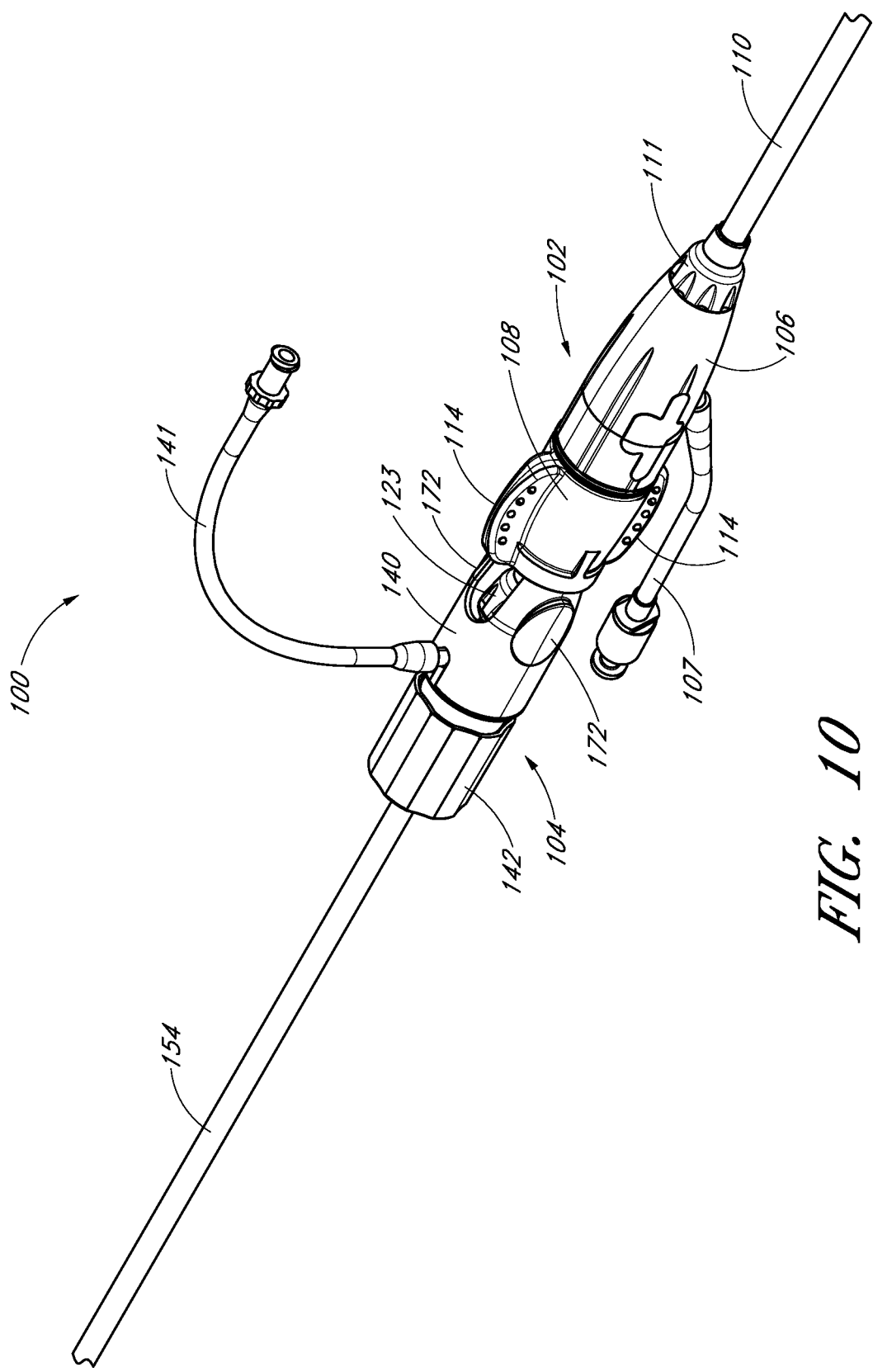
FIG. 10 is a perspective view of the embodiment of the catheter system shown in FIG. 4, showing the delivery catheter after the docking mechanism of the delivery catheter has been engaged with the docking mechanism of the introducer.

FIG. 7 is a perspective view of the embodiment of the delivery catheter 104 of the embodiment of the catheter system 100 shown in FIG. 4. FIGS. 8A and 8B are a first and second exploded assembly view of the embodiment of the delivery catheter 104 shown in FIG. 7. FIG. 9 is a perspective view of the embodiment of the catheter system 100 shown in FIG. 4, showing the delivery catheter 104 before the docking mechanism of the delivery catheter 104 has been engaged with the docking mechanism of introducer 102. FIG. 10 is a perspective view of the embodiment of the catheter system 100 shown in FIG. 4, showing the delivery catheter 104 after the docking mechanism of the delivery catheter 104 has been engaged with the docking mechanism of the introducer 102.

Figure 11:
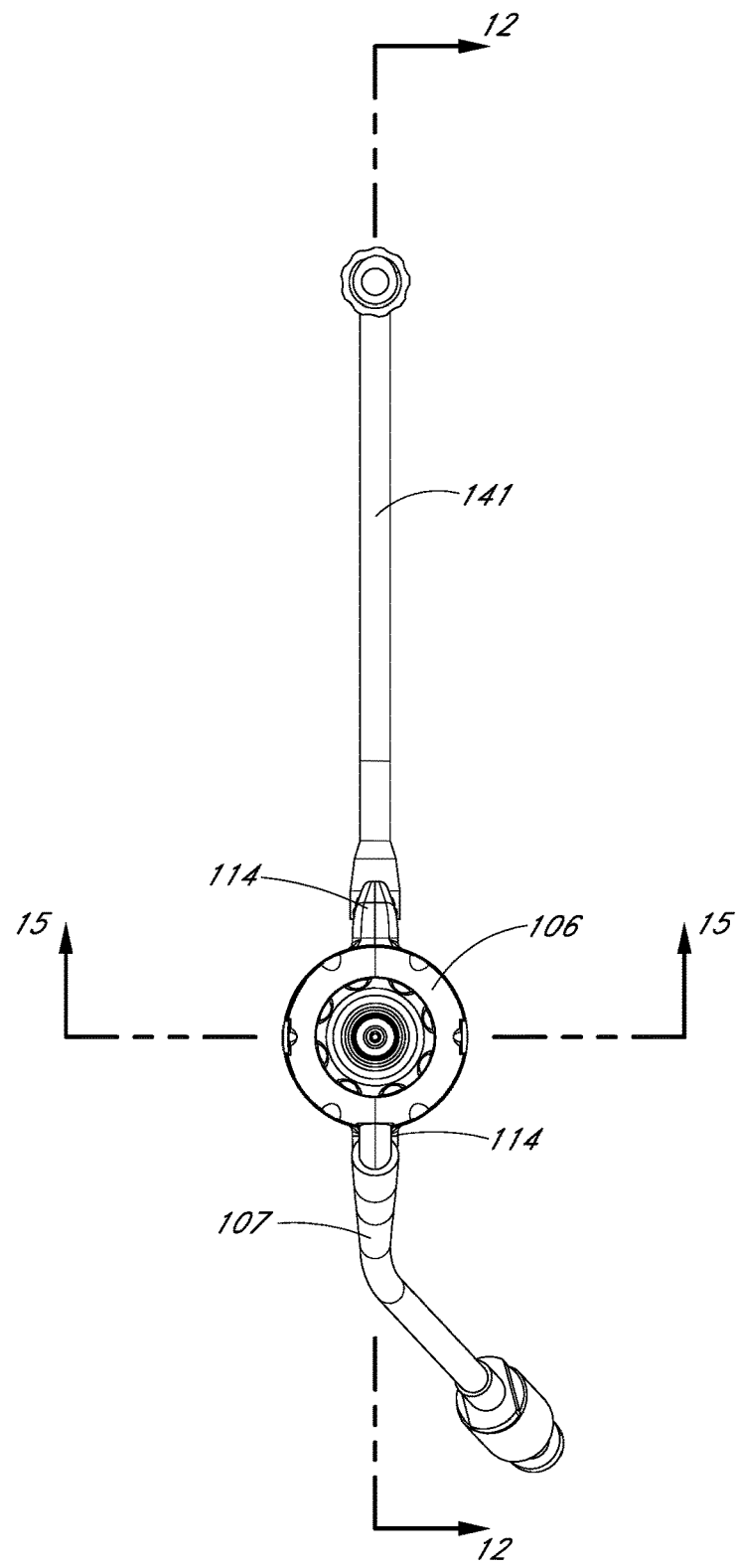
FIG. 11 is an end view of the embodiment of the catheter system shown in FIG. 4.
Figure 12:
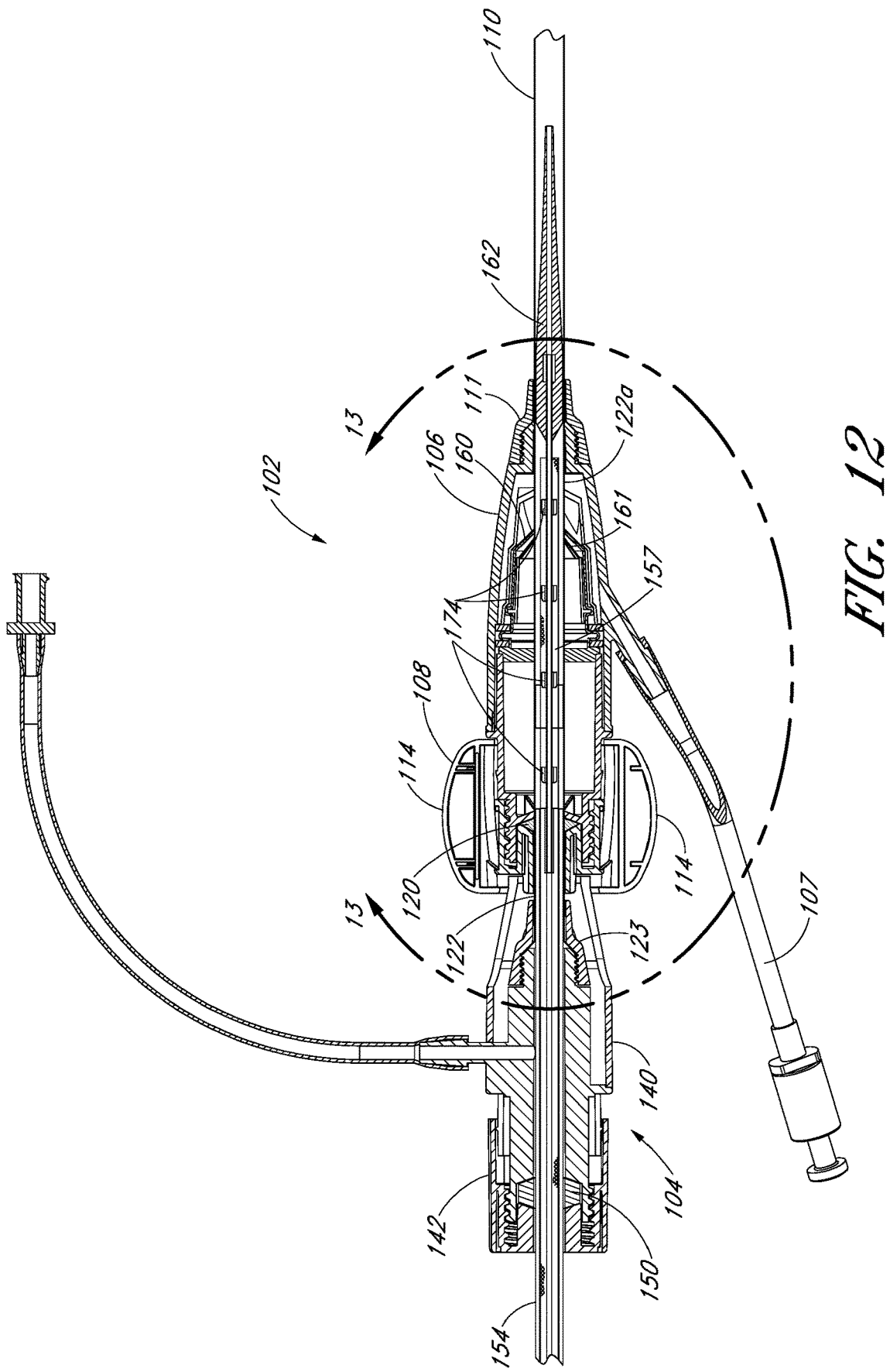
FIG. 12 is a section view of the embodiment of the catheter system shown in FIG. 4, taken through the line 12-12 of FIG. 11.
Figure 13:
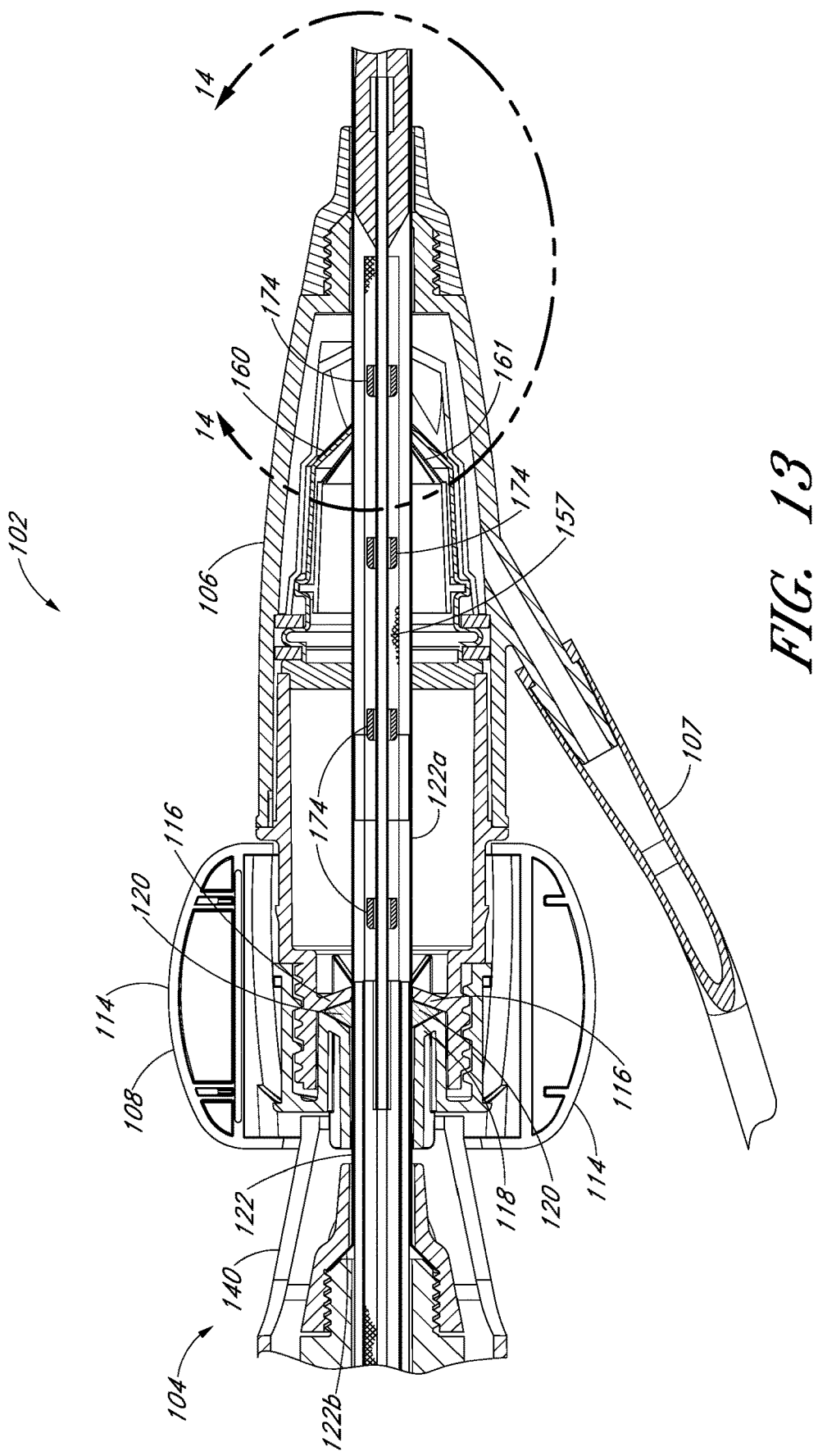
FIG. 13 is an enlarged section view of the embodiment of the catheter system shown in FIG. 4, defined by curve 13-13 of FIG. 12.
Figure 14:
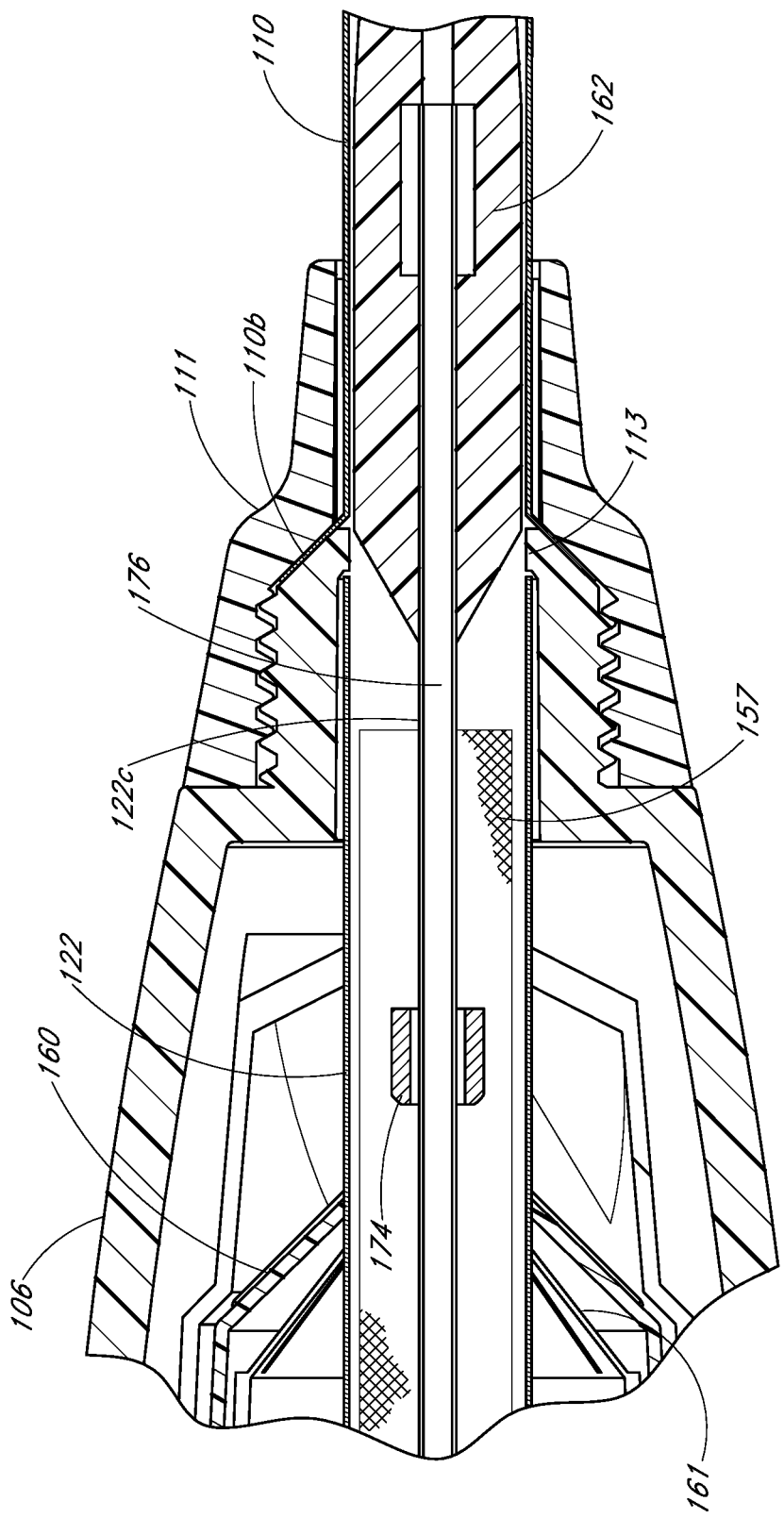
FIG. 14 is an enlarged section view of the embodiment of the catheter system shown in FIG. 4, defined by curve 14-14 of FIG. 13.

FIG. 11 is an end view of the embodiment of the catheter system shown in FIG. 4, with the delivery catheter 104 engaged with the introducer 102. FIG. 12 is a section view of the embodiment of the catheter system 100 shown in FIG. 4, taken through the line 12-12 of FIG. 11. FIG. 13 is an enlarged section view of the embodiment of the catheter system 100 shown in FIG. 4, defined by curve 13-13 of FIG. 12. FIG. 14 is an enlarged section view of the embodiment of the catheter system shown in FIG. 4, defined by curve 14-14 of FIG. 13. Finally, FIG. 15 is a section view of the embodiment of the catheter system shown in FIG. 4, taken through the line 15-15 of FIG. 11.

Figure 15:
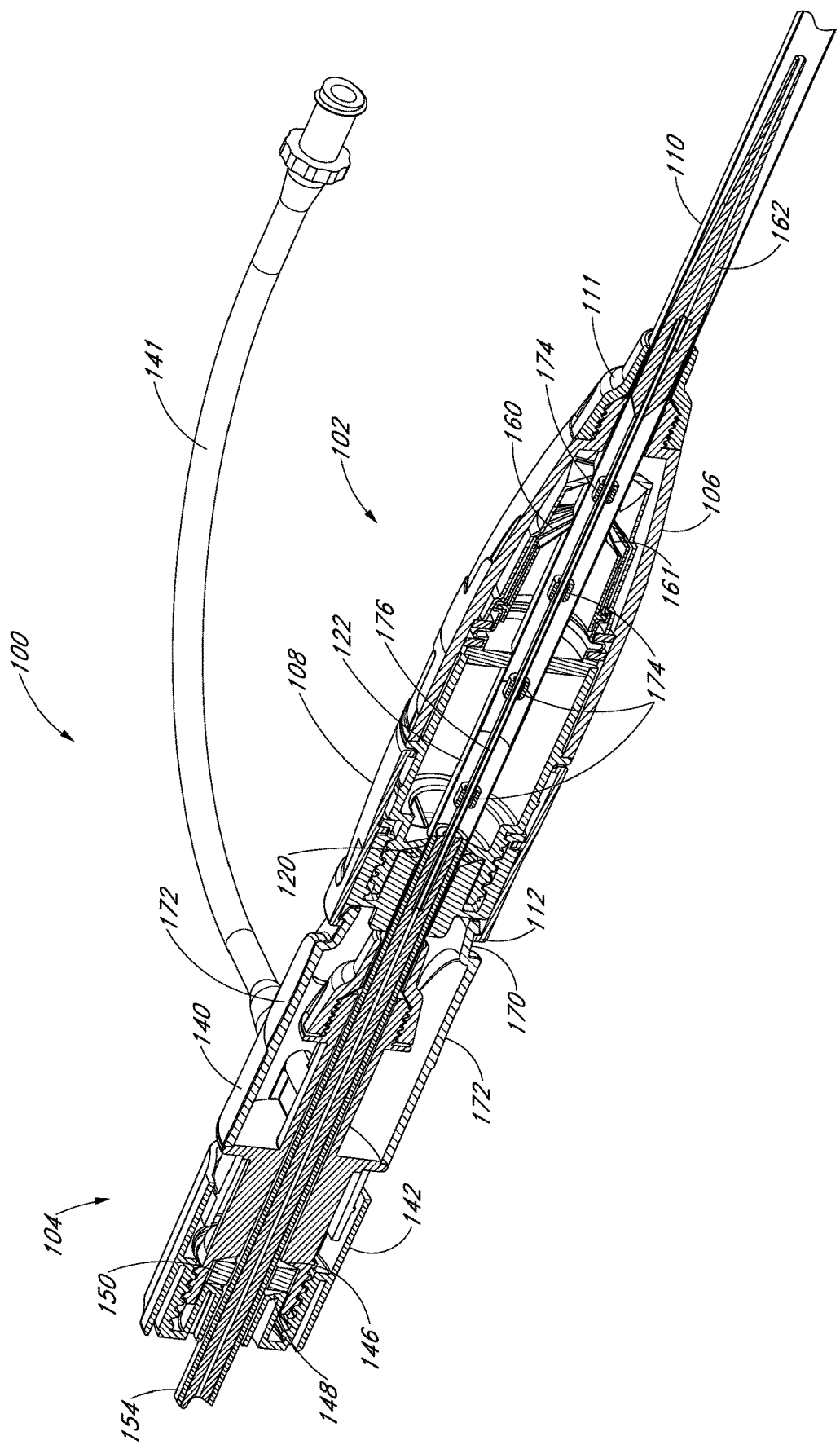
FIG. 15 is a section view of the embodiment of the catheter system shown in FIG. 4, taken through the line 15-15 of FIG. 11.

As shown most clearly in FIGS. 12 and 15, the hub portion 108 of the introducer 102 can have a docking mechanism or flange 112 or can be configured to removably receive or engage with the delivery catheter 104. In some embodiments, as in the illustrated embodiment, the docking mechanism 112 of the introducer 102 can be configured to be a female receiver, configured to receive a male docking member of the catheter 104, as will be described below. In some embodiments, the hub portion 108 can comprise one or more tabs 114 configured to improve a user's grip on the hub portion 108, and ability to rotate the hub portion 108 relative to the main body 106.

With reference to FIGS. 12, 13, and 15, some embodiments of the seal portion of the introducer 102 will be described. As mentioned above, the hub portion 108 can be configured to be threadably engageable with the main body 106. In some embodiments, the main body 108 can define an inner annular surface 116 that can be angled (so as to not be perpendicular to the axial centerline of the catheter system 100). In some embodiments, the surface 116 can be angled approximately 75 degrees relative to the axial centerline of the catheter system 100, or from approximately 65 degrees or less to approximately 80 degrees or more relative to the axial centerline of the catheter system 100. In some embodiments, the surface 116 can be approximately perpendicular to the axial centerline of the catheter system 100.

Similarly, in some embodiments, the hub portion 108 can define an inner annular surface 118 that can be angled so as to not be perpendicular to the axial centerline of the catheter system 100. In some embodiments, the surface 118 of the hub portion 108 can be angled approximately 75 degrees relative to the axial centerline of the catheter system 100, or from approximately 65 degrees or less to approximately 80 degrees or more and relative to the axial centerline of the catheter system 100 in a direction that is opposite to the direction of the angle defined by the surface 116 of the main body 106. In some embodiments, as in the illustrated embodiment, the shape and angular orientation of the surface 118 of the hub portion 108 can approximately mirror the shape and angular orientation of the surface 116 of the main body 106. In some embodiments, the surface 118 can be approximately perpendicular to the axial centerline of the catheter system 100.

An annular seal member 120 can be supported by the introducer 102 and positioned between the surface 116 of the main body 106 and the surface 118 of the hub portion 108. The seal member 120 can be formed from a resilient material, such as silicone, rubber or any other suitable material. The seal member 120 can be configured such that, when the hub portion 108 is threaded onto the main body 106, the surface 118 of the hub portion 108 can be moved axially toward the surface 116 of the main body 106, thereby compressing or squeezing the seal member 120. The relative angles of the surface 116 of the main body 106 and the surface 118 of the hub portion 108 can cause the seal member 120 to be forced against an outer sheath 122 of the delivery catheter 104 or other component of the delivery catheter 104 that is engaged with the introducer 102, thereby creating an adjustable seal between the outer sheath 122 of the delivery catheter 104, which can project distally from an end portion of the delivery catheter 104, and the introducer 102. In some embodiments, the level of seal can be adjusted by tightening or loosening the hub portion 108 of the introducer 102 relative to the main body 106 of the introducer 102. In some embodiments, the introducer 102 can be configured to provide a seal against devices with a profile ranging from 1 Fr to 20 Fr.

Alternatively, in some embodiments, any of the seals or seal portions described herein can be an interference or close tolerance fit between adjacent components such as, without limitation, the outer sheath 122 and one or more inside surfaces of the main body 106 or the hub portion 108 of the introducer 102. In some embodiments, any of the seals or seal portions described herein can be an interference or close tolerance fit between the inner core 154 and one or more inside surfaces of the main body 140 or the hub portion 142 of the catheter 104.

As shown in FIGS. 7, 8A, and 8B, some embodiments of the delivery catheter 104 can comprise a main body 140 and a hub portion 142 threadably engageable with the main body 140. Some embodiments of the delivery catheter 104 can also have an outer sheath 122 supported by the main body 140. In particular, the outer sheath 122 can be removably supported by the main body 140 using a cap 123 threadably supported by the main body 140. Further, in some embodiments, the outer sheath 122 can have an elongate portion 122a extending to any predetermined or desired length.

As mentioned above, in some embodiments, the inside and/or outside diameter of the outer sheath 122 of a delivery catheter 104 can be approximately the same as or similar to the inside and/or outside diameter of the introducer sheath 110. In some embodiments, the elongate portion 122a can be circular in cross-section (as illustrated), or can define any suitable cross-sectional shape such as without limitation triangular, square, hexagonal, octagonal, or polygonal.

The outer sheath 122 can have a flared end portion 122b that can be configured to abut against a fore surface 140a of the main body 140. With reference to FIG. 8A, the elongate portion 122a of the outer sheath 122 can pass through an opening formed in the cap 123 so that the flared portion 122b of the outer sheath 122 can be engaged with and/or overlap an inside surface of the cap 123. In this configuration, the cap 123 supporting the outer sheath 122 can be threadedly engaged with the main body 140 as mentioned above so that the outer sheath 122 is supported by the main body 140.

Additionally, with reference to FIGS. 8A and 8B, a tubular support or spacer 125 can be inserted over the elongate portion 122a of the outer sheath 122 and positioned approximately adjacent to the flared portion 122b of the outer sheath 122. The tubular spacer 125 can improve the fit and, hence, the seal between the outside surface of the outer sheath 122 and the cap 123. The tubular spacer 125 can also provide additional support to the outer sheath 122.

Similar to the hub portion 108 of the introducer 102, the hub portion 142 of the delivery catheter 104 can be configured to be threadably engageable with the main body 140 of the delivery catheter 104. In some embodiments, the main body 140 can define an inner annular surface 146 that can be angled so as to not be perpendicular to the axial centerline of the catheter system 100. In some embodiments, the surface 146 can be angled approximately 75 degrees relative to the axial centerline of the catheter system 100, or from approximately 80 degrees or more to approximately 65 degrees or less relative to the axial centerline of the catheter system 100. In some embodiments, the surface 146 can be approximately perpendicular to the axial centerline of the catheter system 100.

In some embodiments, a second tube 141 can be supported by the main body 140 so as to provide an orifice or access port into the main body 140. The second tube 141 can be used to flush the delivery catheter 104 with saline or other suitable substances at any stage, such as but not limited to prior to the advancement of an endoluminal prosthesis through the delivery catheter 104 and/or introducer 102, or prior to other procedures for which an delivery catheter may be used. The second tube 141 can support any suitable medical connector and/or valve on the distal end thereof.

Similarly, in some embodiments, the hub portion 142 can define an inner annular surface 148 that can be angled so as to not be perpendicular to the axial centerline of the catheter system 100. In some embodiments, the surface 148 of the hub portion 142 can be angled approximately 75 degrees relative to the axial centerline of the catheter system 100, or from approximately 65 degrees or less to approximately 80 degrees or more relative to the axial centerline of the catheter system 100 in a direction that is opposite to the direction of the angle defined by the surface 146 of the main body 140. In some embodiments, the surface 148 can be approximately perpendicular to the axial centerline of the catheter system 100.

Similar to that of the introducer, in some embodiments, a seal or seal portion comprising an annular seal member 150 can be supported by the delivery catheter 104 and positioned between the surface 146 of the main body 140 and the surface 148 of the hub portion 142. The seal member 150 can be formed from a resilient material, such as silicone, rubber or any other suitable material. The seal member 150 can be configured such that, when the hub portion 142 is threaded onto the main body 140, the surface 148 of the hub portion 142 can be moved axially toward the surface 146 of the main body 140, thereby compressing or squeezing the seal member 150. The relative angles of the surface 146 of the main body 140 and the surface 148 of the hub portion 142 can cause the seal member 150 to be forced against the inner core 154 of the delivery catheter 104, thereby creating an adjustable seal between the inner core 154 the outer sheath 122 of the delivery catheter 104.

In some embodiments, the level of seal can be adjusted by tightening or loosening the hub portion 142 of the delivery catheter 104 relative to the main body 140 of the delivery catheter 104. Additionally, in some embodiments, the rotational freedom of inner core 154 of the delivery catheter 104 can be inhibited or prevented by tightening the seal member 150 as described above. Thus, the force exerted by the seal member 150 on the inner core 154 can be adjusted to permit the inner core 154 and/or other components to rotate relative to the main body 140 and hub portion 142 of the delivery catheter 104. As illustrated in FIG. 4, an end portion or cap 158 can be supported at the proximal end of the inner core 154 to facilitate a user's ability to axially slide and/or rotate that inner core 154 relative to the main body 140 and hub portion 142 of the delivery catheter 104. In some embodiments, the cap 158 can have wings or tabs formed thereon to increase the torque or rotational force that can be exerted on the inner core 154. Alternatively, in some embodiments, the seal or seal portion within the catheter 104 can be formed from an interference or close tolerance fit between adjacent components such as, without limitation, the inner core 154 and one or more inside surfaces of the main body 140 or the hub portion 142 of the catheter 104.

In some embodiments, the inner core 154 can have a band or other marking 155 near a distal end thereof. The marking 155 can be sized, positioned, and configured to provide a visual indication to the medical practitioner as to the location of the end portion 154a of the inner core 154 and/or the location of a catheter tip 162 as the inner core 154 is being advanced into or withdrawn from the introducer 102.

In some embodiments, as illustrated most clearly in FIGS. 12 and 13, an additional seal member 160 can be supported by the main body 106 of the introducer 102 to provide an additional seal between the outer sheath 122 of the delivery catheter 104 and the introducer 102. In some embodiments, the seal 160 can be a flap type seal formed from a conically shaped piece of resilient material such as, but not limited to, rubber having one or more slits therein to allow the distal tip 162 and the outer sheath 122 to pass therethrough. In some embodiments, a supported flange 161 can be supported within the main body 106 and positioned behind the seal 160 to support the seal 160 and maintain the position of the seal 160 so that the seal 160 does not become inverted when the delivery catheter 104 is removed from the introducer 102. In some embodiments, the distal tip 162 can be formed from a soft material such as rubber and can be configured to be atraumatic so as to prevent any damage to a patient's vasculature as the catheter 104 is being advanced through the patient's vasculature.

As mentioned above, in some embodiments, as in the illustrated embodiment, the docking mechanism 112 of the introducer 102 can be configured to receive a male docking member or portion of the catheter 104. In particular, with reference to FIGS. 7, 8A and 8B, one or more deflectable tabs 170 can be supported by the main body 140 of the catheter 104. In some embodiments, the tabs 170 can be deflected by pressing or exerting a radial inward force against pads 172, causing the ends of the tabs 170 to move radially inward toward the axial centerline of the main body 104. By deflecting the tabs 170 inwardly, the main body 140 of the catheter 104 can be moved axially into engagement with the hub portion 108 of the introducer 102. In some embodiments, the tabs 170 can be automatically deflected inwardly when the main body 140 of the catheter 104 is moved axially into engagement with the hub portion 108 of the introducer 102. Once the main body 140 of the catheter 104 is moved axially into engagement with the hub portion 108 of the introducer 102 so as to abut against the hub portion 108 of the introducer, the tabs 170 can be released, thereby removably locking the main body 140 of the catheter 104 to the hub portion 108 of the introducer 102.

In this configuration, the catheter 104 can be axially engaged with or locked to the introducer 102 so that a user can axially manipulate the introducer 102 and the catheter 104 simultaneously. Additionally, in some embodiments, in this configuration, as discussed above, the catheter system 100 can be configured such that at least the inner core 154 of the catheter 104 can be rotated relative to the main body 140 of the catheter 104 and the introducer 102.

In some embodiments, as shown in FIGS. 7, 8A, and 8B, the inner core 154 can have a central tube or wire 176 configured to support a stent, such as stent 157 illustrated in FIGS. 7 and 12-14. Additionally, one or more beads or tabs 174 can be formed on or supported by the central tube or wire 176. The tabs 174 can be configured to increase the axial support or connection between the inner core 154 and an endoluminal prosthesis supported by the central tube 176 when the prosthesis is supported in a collapsed configuration by the central tube 176. In some embodiments, the catheter 104 can be configured such that an opening passes through the distal tip 162, the central tube 176, and the inner core 124. The opening can be configured so that at least the distal tip 162, the central tube 176, and the inner core 124 can be advanced over a guidewire positioned within a patient's vasculature, such as is described in U.S. patent application Ser. No. 12/101,863 filed on Apr. 11, 2008 (titled: BIFURCATED GRAFT DEPLOYMENT SYSTEMS AND METHODS), which application is hereby incorporated by reference in its entirety as if fully set forth herein.

Additionally, in some embodiments (not illustrated), the tabs 174 can be sized, spaced, and otherwise configured to provide axially support to multiple individual stent segments. For example, without limitation, multiple independent or tethered stent segments can be positioned within a tubular or bifurcated graft, and the stent graft can be positioned relative to the tabs 174 such that the tabs 174 are positioned between the stent segments. This arrangement can reduce the overall diameter of the outer sheath 122, the introducer sheath 110, and other components comprising the catheter system, can enhance the axial support provided by the tabs 174 to the endoluminal prosthesis, and can allow for a more uniform distribution of support forces between the tabs 174 and the endoluminal prosthesis. In some embodiments, the tabs 174 can be sized, spaced, and otherwise configured so as to be positioned adjacent to the links, bends, loops, and/or other connectors formed in a tubular or bifurcated stent, such as the links, bends, loops, and/or other connectors comprising the embodiments of the stents disclosed in U.S. Pat. No. 6,077,296 titled ENDOLUMINAL VASCULAR PROSTHESIS, which patent is hereby incorporated by reference as if fully set forth herein.

With reference to FIGS. 13-15, the outer sheath 122 of the deployment catheter 104 can be advanced into an axial opening within the introducer 102 when the deployment catheter 104 is engaged with the introducer 102. In some embodiments, the outer sheath 122 can be sized and configured such that the distal end portion 122c of the outer sheath 122 can terminate within the introducer 102 prior or proximal to the proximal end or flared portion 110b of the introducer sheath 110. Although not required, the introducer 102 can have a constricted portion 113 formed in the main body 106 of the introducer. In some embodiments, as shown most clearly in FIG. 14, the catheter system 100 can be configured such that the distal end 122c of the outer sheath 122 terminates prior to or approximately adjacent to a constricted portion 113 of the main body 106 of the introducer 102.

In some embodiments (not illustrated), the distal end portion 122c of the outer sheath 122 can be positioned near to or approximately adjacent to the proximal end portion or the flared portion 110b of the introducer sheath 110, regardless of whether the catheter 104 has a constricted portion 113. The inner diameter of the constricted portion 113 can be approximately the same as the inner diameter of the outer sheath 122 and/or the inner diameter of the introducer sheath 110.

Therefore, in some embodiments, the outer sheath 122 of the catheter 104 and the introducer sheath 110 can be configured to provide a lumen having a generally uniform cross-sectional size through the catheter system through which the endoluminal prosthesis can be advanced. In some embodiments, the lumen through the catheter system 100 through which the endoluminal prosthesis can be advanced can be substantially continuous, so that the endoluminal prosthesis can be advanced through the catheter system 100 without the prosthesis being obstructed by or snagging on any components or features of the catheter system 100 as it is being advanced. In some embodiments, the lumen can be substantially continuous but have short gaps on the order of approximately 1 mm to approximately 3 mm in the lumen such as, without limitation, adjacent to the distal end of the outer sheath 122 of the catheter 104 and/or adjacent to the proximal or flared end 110*b* of the introducer sheath 110. For example, in some embodiments, short gaps can be formed adjacent to the distal end of the outer sheath 122 of the catheter 104 and/or adjacent to the proximal or flared end 110*b* of the introducer sheath 110 as some components comprising the catheter system 100 are threadedly engaged with other components comprising the catheter system 100. Further, in some embodiments, one or more surfaces of other components comprising the catheter 104 or the introducer 102 in addition to the outer sheath 122 and the introducer sheath 110, such as without limitation the constricted portion 113 of the main body 106 of the introducer 102 as discussed above, can form portions of the lumen through the catheter system 100.

In some embodiments, the outer sheath 122 can constrain or restrain an endoluminal prosthesis supported by the central tube 176 as described above. In this configuration, as the catheter tip 162, central core 154, and an endoluminal prosthesis (such as, but not limited to, stent 157 illustrated in FIGS. 7 and 12-14) are advanced through the outer sheath 122, the outer sheath 122 can restrain the endoluminal prosthesis and prevent the endoluminal prosthesis from expanding before reaching the target position within the patient's vasculature. Additionally, the catheter system 100 can be configured such that, as the catheter tip 162, central core 154, and endoluminal prosthesis are advanced past the distal end 122*c* of the outer sheath 122, the constricted portion 113 and, subsequently, the introducer sheath 110 can radially restrain the endoluminal prosthesis as the endoluminal prosthesis is advanced through the introducer sheath 110.

In some embodiments, the endoluminal prosthesis or the stent 157 can be a tubular stent, a bifurcated stent, or any other desirable stent, graft, stent graft, or endoluminal prosthesis (collectively referred to herein as stent or stents), including without limitation any of the stents or grafts disclosed in U.S. patent application Ser. No. 12/101,863 referenced above and incorporated herein by reference as if fully set forth herein. Accordingly, in some embodiments, the catheter system 100 or catheter 104 can be configured to deploy any suitable or desirable stent or stents.

Thus, in this configuration, the endoluminal prosthesis can be transferred from the outer sheath 122 to the introducer sheath 110. In this arrangement, using the introducer sheath 110 as the restraint can allow the outside diameter of the introducer sheath 110 to be reduced, which can minimize trauma to the patient's vasculature and assist in the deployment of the endoluminal prosthesis.

Many embodiments of the docking mechanism and catheter system have been described in connection with FIGS. 1-15. It will apparent to one of ordinary skill in the art that there are many potential embodiments of a permanent or removable docking mechanism that may be suitable for medical use and which are contemplated herein. For example, in some embodiments, a nut-screw combination could be used to connect the introducer sheath and the catheter. As another example, a bayonet style locking mechanism, such as is used for camera lenses, can also be used. In some embodiments, any of the components or features of some embodiments of the catheters disclosed herein or other catheters available in the field can be combined to form additional embodiments, all of which are contemplated herein.

While the above description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

What is claimed is:

1. A catheter system comprising:
an introducer comprising a main body and a tubular introducer sheath projecting from the main body; and
a catheter comprising a main body and an outer sheath projecting from the main body, the outer sheath configured to be at least partially advanced through the main body of the introducer;
wherein when the introducer and the catheter are axially locked, there is rotational freedom between the catheter and the introducer while a stent or a stent graft is released from the catheter system; and
wherein the catheter further comprises an inner core that is configured to be advanceable through the main body of the catheter and the outer sheath; and
wherein the inner core is configured to be advanceable over a guidewire.

2. The catheter system of claim 1, wherein the stent or the stent graft is axially supported by the catheter.

3. The catheter system of claim 1, wherein the outer sheath of the catheter does not overlap any portion of the tubular introducer sheath when the catheter is axially locked with the introducer.

4. The catheter system of claim 1, wherein a distal end portion of the outer sheath is positioned approximately adjacent to a proximal end portion of the tubular introducer sheath when the catheter is axially locked with the introducer.

5. The catheter system of claim 1, wherein an inner diameter of the outer sheath is approximately the same as an inner diameter of the tubular introducer sheath.

6. The catheter system of claim 1, wherein the outer sheath and the tubular introducer sheath form a lumen having a substantially uniform cross-sectional size through the catheter system.

7. The catheter system of claim 1, wherein the catheter comprises at least one deflectable tab supported by the main body of the catheter and the introducer comprises at least one flange, and the at least one deflectable tab is configured to selectively engage with the at least one flange so as to axially engage the catheter with the introducer.

8. The catheter system of claim 7, wherein the catheter is configured to disengage from the introducer by deflecting the at least one deflectable tab radially inwardly toward an axial centerline of the catheter and axially retracting the catheter away from the introducer.

9. The catheter system of claim 1, wherein when the introducer and the catheter are axially locked, axial movement of either of the introducer and the catheter in a proximal or a distal direction will cause a simultaneous and equal axial movement of the other of the introducer and the catheter so as to prevent the movement of either of the introducer and the catheter relative to the other of the introducer and the catheter.

10. The catheter system of claim 1, further comprising a locking element configured to selectively lock the catheter to the introducer in an axial direction such that, when the introducer and the catheter are axially locked, axial movement of either of the introducer and the catheter in a proximal or a distal direction will cause a simultaneous and equal axial movement of the other of the introducer and the catheter so as to prevent the movement of either of the introducer and the catheter relative to the other of the introducer and the catheter.

11. The catheter system of claim 1, wherein the catheter system is configured to prevent an outer sheath of the catheter from advancing into the introducer sheath when the catheter has reached a fully advanced position in the introducer.

12. A catheter system comprising:
   an introducer comprising a main body and a tubular introducer sheath projecting from the main body; and
   a catheter comprising a main body and an outer sheath projecting from the main body, the outer sheath configured to be at least partially advanced through the main body of the introducer;
   wherein when the introducer and the catheter are axially locked, the catheter is freely rotatable within the introducer sheath;
   wherein the catheter further comprises at least one deflectable tab supported by the main body of the catheter, the at least one deflectable tab configured to selectively engage the introducer by distally advancing a distal free end of each of the at least one deflectable tab into a proximal end of the main body of the introducer;
   wherein the catheter further comprises an inner core that is configured to be advanceable through the main body of the catheter and the outer sheath; and
   wherein the inner core is configured to be advanceable over a guidewire.

13. The catheter system of claim 12, further comprising a stent or a stent graft axially supported by the catheter.

14. The catheter system of claim 12, wherein the catheter is configured to be disengaged from the introducer by deflecting the at least one deflectable tab radially inwardly toward an axial centerline of the catheter.

15. The catheter system of claim 12, wherein the outer sheath and the tubular introducer sheath form a lumen having a substantially uniform cross-sectional size through the catheter system through which a stent or a stent graft can be advanced.

16. The catheter system of claim 12, wherein the introducer comprises at least one flange, the at least one deflectable tab being configured to selectively engage with the at least one flange so as to axially engage the catheter with the introducer.

17. A catheter system comprising:
   an introducer comprising a main body and a tubular introducer sheath projecting from the main body, the tubular introducer sheath comprising a proximal end portion extending from the main body and a distal end portion;
   a catheter comprising a main body and an outer sheath projecting from the main body, the outer sheath comprising a proximal end portion and a distal end portion, the outer sheath configured to be at least partially advanced through the main body of the introducer; and
   wherein when the introducer and the catheter are axially locked, the catheter is fully rotatable within the introducer sheath;
   wherein the tubular introducer sheath is configured to directly radially restrain a stent or a stent graft after the stent or the stent graft has been axially advanced past the distal end portion of the outer sheath and the proximal end portion of the tubular introducer sheath;
   wherein the catheter further comprises an inner core that is configured to be advanceable through the main body of the catheter and the outer sheath; and
   wherein the inner core is configured to be advanceable over a guidewire.

18. The catheter system of claim 17, further comprising a stent or a stent graft axially supported by the catheter.

19. The catheter system of claim 17, wherein a distal end portion of the outer sheath is positioned approximately adjacent to a proximal end portion of the tubular introducer sheath when the catheter is axially engaged with the introducer.

20. The catheter system of claim 17, wherein the outer sheath and the tubular introducer sheath form a lumen having a substantially uniform cross-sectional size through the catheter system through which the stent or the stent graft can be advanced.

21. The catheter system of claim 17, wherein the catheter comprises at least one deflectable tab and the introducer comprises at least one flange, and the at least one deflectable tab is configured to selectively engage with the at least one flange so as to axially engage the catheter with the introducer.

* * * * *